United States Patent
Till et al.

(10) Patent No.: US 8,147,816 B2
(45) Date of Patent: *Apr. 3, 2012

(54) PRESBYOPIA TREATMENT BY LENS ALTERATION

(75) Inventors: Jonathan S. Till, Roanoke, VA (US); Ronald D. Blum, Roanoke, VA (US); William R. Burns, North Richland Hills, TX (US)

(73) Assignee: Encore Health, LLC, Roanoke, VA (US)

( * ) Notice: Subject to any disclaimer, the term of this patent is extended or adjusted under 35 U.S.C. 154(b) by 1105 days.

This patent is subject to a terminal disclaimer.

(21) Appl. No.: 11/946,659

(22) Filed: Nov. 28, 2007

(65) Prior Publication Data

US 2008/0139990 A1    Jun. 12, 2008

Related U.S. Application Data

(63) Continuation-in-part of application No. 11/135,271, filed on May 24, 2005, now Pat. No. 7,914,815, and a continuation-in-part of application No. 10/050,879, filed on Jan. 18, 2002, now Pat. No. 6,923,955, application No. 11/946,659, which is a continuation-in-part of application No. 11/010,436, filed on Dec. 14, 2004, now Pat. No. 7,935,332, which is a continuation-in-part of application No. 10/050,879, application No. 11/946,659, which is a continuation-in-part of application No. 10/969,868, filed on Oct. 22, 2004, now abandoned, said application No. 10/050,879 and a continuation-in-part of application No. 09/930,287, filed on Aug. 16, 2001, now abandoned.

(60) Provisional application No. 60/861,262, filed on Nov. 28, 2006, provisional application No. 60/907,734, filed on Apr. 16, 2007, provisional application No. 60/924,686, filed on May 29, 2007, provisional application No. 60/574,211, filed on May 26, 2004, provisional application No. 60/262,423, filed on Jan. 19, 2001, provisional application No. 60/225,659, filed on Aug. 16, 2000.

(51) Int. Cl.
    *A61K 31/74*    (2006.01)
(52) U.S. Cl. .................................... 424/78.04
(58) Field of Classification Search .................. None
    See application file for complete search history.

(56) References Cited

U.S. PATENT DOCUMENTS 817,630 A    4/1906    Delaunay-Belleville
(Continued)

FOREIGN PATENT DOCUMENTS

EP    0 369 880    5/1990
(Continued)

OTHER PUBLICATIONS

Morris Jr. Recent advances in arginine metabolism; roles and regulation of the arginases. British Journal of Pharmacology, E-Pub Jun. 5, 2009, 157(6):922-930.

(Continued)

*Primary Examiner* — Carlos Azpuru
(74) *Attorney, Agent, or Firm* — Kilpatrick Townsend & Stockton LLP

(57) ABSTRACT

Embodiments of the present invention relate to methods and pharmacological or biological compositions to treat presbyopia in the human eye. According to the embodiments, pharmacological or biological compositions may be applied to or injected into an eye to effect a change in the accommodative ability of the eye by the breaking and reduction of lenticular bonds in the eye that may be responsible for presbyopia. The compositions may be applied in an inactive state and subsequently be activated to achieve a therapeutic effect. The application of energy may be used to either break the oxidized lenticular bonds and/or to activate one or more of the pharmacological or biological agents. The energy may be used in a focus treatment pattern to affect a change in the refractive characteristics of the eye and thereby reduce inherent optical distortions.

5 Claims, 6 Drawing Sheets

U.S. PATENT DOCUMENTS

| | | | |
|---|---|---|---|
| 3,238,224 A | 3/1966 | Ohara et al. |
| 3,855,240 A | 12/1974 | Mueller |
| 4,210,667 A | 7/1980 | Sarges et al. |
| 4,755,528 A | 7/1988 | DuPriest et al. |
| 5,395,356 A | 3/1995 | King et al. |
| 5,459,133 A | 10/1995 | Neufeld |
| 5,465,737 A | 11/1995 | Schachar |
| 5,466,680 A | 11/1995 | Rudy |
| 5,476,515 A | 12/1995 | Keiman et al. |
| 5,488,050 A | 1/1996 | Neufeld |
| 5,503,165 A | 4/1996 | Schachar |
| 5,527,774 A | 6/1996 | Girard |
| 5,529,076 A | 6/1996 | Schachar |
| 5,624,955 A | 4/1997 | Nagasawa et al. |
| 5,665,770 A | 9/1997 | Terao et al. |
| 5,686,450 A | 11/1997 | Hellberg et al. |
| 5,688,828 A | 11/1997 | Hellberg et al. |
| 5,691,379 A | 11/1997 | Ulrich et al. |
| 5,722,952 A | 3/1998 | Schachar |
| 5,772,952 A | 6/1998 | Allen et al. |
| 5,817,630 A | 10/1998 | Hoffmann et al. |
| 5,843,184 A | 12/1998 | Cionni |
| 5,869,468 A | 2/1999 | Freeman |
| 5,874,455 A | 2/1999 | Terao et al. |
| 5,888,243 A | 3/1999 | Silverstrini |
| 6,007,510 A | 12/1999 | Nigam |
| 6,013,462 A | 1/2000 | Kauvar et al. |
| 6,030,950 A | 2/2000 | Ohlenschlager |
| 6,063,116 A | 5/2000 | Kelleher |
| 6,214,044 B1 | 4/2001 | Silverstrini |
| 6,313,164 B1 | 11/2001 | Fujita et al. |
| 6,339,102 B1 | 1/2002 | Meyerhoff et al. |
| 6,387,945 B2 | 5/2002 | Packer et al. |
| 6,472,541 B2 | 10/2002 | Tsien et al. |
| 6,664,287 B2 | 12/2003 | Avery et al. |
| 6,703,039 B2 | 3/2004 | Xia et al. |
| 6,743,779 B1 | 6/2004 | Unger et al. |
| 6,923,955 B2 | 8/2005 | Till |
| 7,164,943 B2 | 1/2007 | Roy |
| 2002/0025311 A1 | 2/2002 | Till |
| 2002/0035243 A1 | 3/2002 | Imfeld et al. |
| 2003/0187058 A1 | 10/2003 | Hasselwander et al. |
| 2003/0228299 A1 | 12/2003 | Droy-Lefaix et al. |
| 2004/0044227 A1 | 3/2004 | Klatt et al. |
| 2004/0092586 A1 | 5/2004 | Ogata et al. |
| 2005/0101677 A1 | 5/2005 | Till |
| 2005/0112113 A1 | 5/2005 | Till |
| 2005/0130881 A1 | 6/2005 | Shashoura et al. |
| 2005/0137124 A1 | 6/2005 | Castillejos |
| 2005/0171212 A1 | 8/2005 | Gierhart et al. |
| 2005/0287201 A1 | 12/2005 | Till |
| 2006/0177430 A1 | 8/2006 | Bhushan |
| 2006/0188492 A1 | 8/2006 | Richardson et al. |
| 2007/0055070 A1 | 3/2007 | Lawrence |
| 2007/0207116 A1 | 9/2007 | Brown |
| 2007/0293562 A1 | 12/2007 | Mylari et al. |
| 2008/0038316 A1 | 2/2008 | Wong et al. |
| 2008/0213239 A1 | 9/2008 | Morris |
| 2009/0082281 A1 | 3/2009 | Shashoua |
| 2009/0093541 A1 | 4/2009 | Ogata |
| 2009/0124683 A1 | 5/2009 | Garner et al. |
| 2009/0192212 A1 | 7/2009 | Garner et al. |
| 2009/0227677 A1 | 9/2009 | Garner et al. |
| 2010/0098653 A1 | 4/2010 | Yu et al. |

FOREIGN PATENT DOCUMENTS

| | | |
|---|---|---|
| WO | WO 93/25166 | 12/1993 |
| WO | WO 02/13863 | 2/2002 |
| WO | WO 03/084532 | 10/2003 |
| WO | WO 2004/028536 | 4/2004 |
| WO | WO 2006/047080 | 5/2006 |
| WO | WO 2008/120070 | 10/2008 |

OTHER PUBLICATIONS

PubChem Compound Summary CID 863 lipoamide (Sep. 16, 2004) (Retrieved from the internet Nov. 13, 2010; http://pubchem.ncbi.nlm.nih.gov/summary/summary.cgi?cid=863.

Salceda, et al. L-arginine uptake in normal and diabetic rat retina and retinal pigment epithelium. Neurochem Res., 2008, 33(8):1541-1545.

Stuehr et al. Nw-Hydroxy-L-arginine is an intermediate in the Biosynthesis of nitric Oxide from L-Arginine. The Journal of Biological Chemistry 1991, 266(10):6259-6263.

Truscott, R. J. 2000. Age-related nuclear cataract: a lens transport problem. *Ophthalmic research* 32: 185-194.

Giblin FJ, et al. 1979, The effects of X-irradiation on lens reducing systems. *Investigative Ophthalmology & Visual Science* 18:468-475.

Halhal M, et al. 2004. Iontophoresis: from the lab to the bed side. Exp Eye Res 78(3)751-57.

Kramár P, et al. 1987. Thermal cataract formation in rabbits. NCBI Pubmed abstract, PMID: 3426637, abstract of Bioelectromagnetics 8:397-406.

Lee V & Bundgaard H. 1992. Improved Ocular Drug Delivery with Prodrugs. In: Sloan K, ed. Produgs: Topical and Ocular Drug Delivery, vol. 53, p. 233.

Lipman RM, et al. 1988. Cataracts induced by Microwave and Ionizing Radiation. NCBI Pubmed abstract, PMID: 3068822, abstract of Surv. Ophthalmol 33:200-210.

Newell, 1996. Ophthalmology: Principles and Concepts St. Louis: Mosby-Year Book St. Louis, p. 83.

Sarraf D & Lee DA. 1994. The Role of Iontophoresis in Ocular Drug Delivery. J Ocul Pharmacol 10(1):69-81.

Willner I & Zehavy E. 1994. Activation of Glutathione Reducase by Light: A Novel Approach to Design Redox Photo-Enzymes. Angew Chem Int Ed Engl 33(5):581-83.

Krumdieck et al.: Mechanism of Homocysteine Toxicity on Connective Tissues: Implications for the Morbidity of Aging, J. Nutr. 2000, 130 (2S suppl):365S-368S.

Krueger, Ronald R., MD, MSE, et al., "Experimental increase in accommodative potential after neodymium: yttrium-aluminum-garnet laser photodisruption of paired cadaver lenses", Ophthalmology (2001), pp. 108:2122-2129.

Spector, Abraham, et al., "Thioredoxin Fragment 31-36 is Reduced by Dihydrolipoamide and Reduces Oxidized Protein", Biochemical and Biophysical Research Communications, vol. 150, No. 1, 1988, pp. 156-162.

Bron, A.J., et al. "The Ageing Lens" Ophthalmologica (2000) 214(1):86-104.

Hoenders, H.J., et al. "Lens proteins and aging" J Gerontol (May 1983) 38(3):278-86.

Moffat, B.A., et al. "Age-related Changes in the Kinetics of Water Transport in Normal Human Lenses" Exp. Eye Res. (1999) 69(6):663-69.

Phelps-Brown, N.A., et al. "Nutritional supplements and the eye" Eye (1998) 12:127-33.

U.S. Appl. No. 12/815,586, filed Jun. 15, 2010, Garner et al.
U.S. Appl. No. 12/815,526, filed Jun. 15, 2010, Garner et al.

Al-Ghoul, K. J., R. K. Nordgren, A. J. Kuszak, C. D. Freel, M. J. Costello, and J. R. Kuszak. 2001. Structural evidence of human nuclear fiber compaction as a function of ageing and cataractogenesis. *Experimental eye research* 72: 199-214.

Applegate, M. A., K. M. Humphries, and L. I. Szweda. 2007. Reversible Inhibition of alpha-Ketoglutarate Dehydrogenase by Hydrogen Peroxide: Glutathionylation and Protection of Lipoic Acid. *Biochemistry*.

Argirova, M., M. Kleine-Reidick, and W. Breipohl. 2004. Redox status of the eye lens: a regional study. *Cell biochemistry and biophysics* 41: 381-390.

Ariga T, et al. 2000. Antithrombotic and antineoplastic effects of phyto-organosulfur compounds. Biofactors. 13(1-4):251-5.

Arora A, et al. 2004. Reversal of P-glycoprotein-mediated multidrug resistance by diallyl sulfide in K562 leukemic cells and in mouse liver. Carcinogenesis. 25(6):941-9. Epub Jan. 16, 2004.

Asmellash S, et al. 2005. Modulating the endoplasmic reticulum stress response with trans-4,5-dihydroxy-1,2-dithiane prevents chemically induced renal injury in vivo. Toxicol Sci. 88(2):576-84. Epub Sep. 8, 2005.

Baghieri, S. and M. H. Garner. 1992. Na,K-ATPase and phospholipid degradation in bovine and human lenses. *Current eye research* 11: 459-467.

Belloir C, et al. 2006. Protective effects of garlic sulfur compounds against DNA damage induced by direct- and indirect-acting genotoxic agents in HepG2 cells. Food Chem Toxicol. 44(6):827-34.
Bilska, A., and L. Wlodek. 2005. Lipoic acid—the drug of the future? Pharmacol Rep 57: 570-577.
Bilska, A., M. Dubiel, M. Sokolowska-Jezewicz, E. Lorenc-Koci, and L. Wlodek. 2007. Alpha-lipoic acid differently affects the reserpine-induced oxidative stress in the striatum and prefrontal cortex of rat brain. *Neuroscience* 146: 1758-1771.
Bitar, M. S., S. Wahid, C. W. Pilcher, E. Al-Saleh, and F. Al-Mulla. 2004. Alpha-lipoic acid mitigates insulin resistance in Goto-Kakizaki rats. *Hormone and metabolic research. Hormon- und Stoffwechselforschung* 36: 542-549.
Blanco, R. A., T. R. Ziegler, B. A. Carlson, P. Y. Cheng, Y. Park, G. A. Cotsonis, C. J. Accardi, and D. P. Jones. 2007. Diurnal variation in glutathione and cysteine redox states in human plasma. *The American journal of clinical nutrition* 86: 1016-1023.
Blankenship, T. N., J. F. Hess, and P. G. FitzGerald. 2001. Development- and differentiation-dependent reorganization of intermediate filaments in fiber cells. *Investigative ophthalmology & visual science* 42: 735-742.
Bonomi, L et al. 1990. Evaluation of the 701 interzeag lens opacity meter. Graefe's Arch Clin Exp Ophthalmol 228(5):447-9.
Borja, D et al. 2008. Optical Power of the Isolated Human Crystalline Lens. Invest Ophthalmol Vis Sci 49(6):2541-8.
Brunkener, M., and S. D. Georgatos. 1992. Membrane-binding properties of filensin, a cytoskeletal protein of the lens fiber cells. *Journal of cell science* 103 ( Pt 3): 709-718.
Bustamante, J., et al., 1998. α-Lipoic Acid in Liver Metabolism and Disease. *Free Radical Biology & Medicine* 24: No. 6 1023-1039.
Cagini, C. MD, et al. 2010. Study of alpha-lipoic acid penetration in the human aqueous humour after topical administration. Clinical and Experimental Ophthalmology "Accepted Article" doi: 10.1111/j.1442-9071.2010.02319.x.
Cenedella, R. J. 1998. Prenylation of proteins by the intact lens. *Investigative ophthalmology & visual science* 39: 1276-1280.
Croft, M. A., A. Glasser, G. Heatley, J. McDonald, T. Ebbert, N. V. Nadkarni, and P. L. Kaufman. 2006. The zonula, lens, and circumlental space in the normal iridectomized rhesus monkey eye. *Investigative ophthalmology & visual science* 47: 1087-1095.
Croft, M. A., and P. L. Kaufman. 2006. Accommodation and presbyopia: the ciliary neuromuscular view. *Ophthalmology clinics of North America* 19: 13-24, v.
Dubbelman, M., G. L. Van der Heijde, H. A. Weeber, and G. F. Vrensen. 2003. Changes in the internal structure of the human crystalline lens with age and accommodation. *Vision research* 43: 2363-2375.
Eason, R. C., H. E. Archer, S. Akhtar, and C. J. Bailey. 2002. Lipoic acid increases glucose uptake by skeletal muscles of obese-diabetic ob/ob mice. *Diabetes Obes Metab* 4: 29-35.
Egan, D., P. James, D. Cooke, and R. O'Kennedy. 1997. Studies on the cytostatic and cytotoxic effects and mode of action of 8-nitro-7-hydroxycoumarin. *Cancer letters* 118: 201-211.
Finn, G., B. Creaven, and D. Egan. 2003. Modulation of mitogen-activated protein kinases by 6-nitro-7-hydroxycoumarin mediates apoptosis in renal carcinoma cells. *European journal of pharmacology* 481: 159-167.
Finn, G. J., B. S. Creaven, and D. A. Egan. 2004. A study of the role of cell cycle events mediating the action of coumarin derivatives in human malignant melanoma cells. *Cancer letters* 214: 43-54.
Flammer J, Bebie H. 1987. Lens Opacity Meter: a new instrument to quantify lens opacity. Ophthalmologica 195(2):69-72.
Furuta, T., S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. *Proceedings of the National Academy of Sciences of the United States of America* 96: 1193-1200.
Gail MH & You WC. 2006. A factorial trial including garlic supplements assesses effect in reducing precancerous gastric lesions. J Nutr. 136(3 Suppl):813S-815S.
Garner, M. H., and J. Horwitz. 1994. Catalytic subunit isoforms of mammalian lens Na,K-ATPase. *Current eye research* 13: 65-77.

Garner, M. H., and Y. Kong. 1999. Lens epithelium and fiber Na,K-ATPases: distribution and localization by immunocytochemistry. *Investigative ophthalmology & visual science* 40: 2291-2298.
Garner, M. H., and J. R. Kuszak. 1993. Cations, oxidants, light as causative agents in senile cataracts. *Puerto Rico health sciences journal* 12: 115-122.
Garner, M. H., and A. Spector. 1980. Selective oxidation of cysteine and methionine in normal and senile cataractous lenses. *Proceedings of the National Academy of Sciences of the United States of America* 77: 1274-1277.
Garner, M. H. 1994. Na,K-ATPases of the lens epithelium and fiber cell: formation of catalytic cycle intermediates and Na+: K+ exchange. *Experimental eye research* 58: 705-718.
Gilmore WJ & Kirby GM. 2004. Endoplasmic reticulum stress due to altered cellular redox status positively regulates murine hepatic CYP2A5 expression. J Pharmacol Exp Ther. 308(2):600-8. Epub Nov. 10, 2003.
Glasser, A., and M. C. Campbell. 1999. Biometric, optical and physical changes in the isolated human crystalline lens with age in relation to presbyopia. *Vision research* 39: 1991-2015.
Goulielmos, G., F. Gounari, S. Remington, S. Muller, M. Haner, U. Aebi, and S. D. Georgatos. 1996. Filensin and phakinin form a novel type of beaded intermediate filaments and coassemble de novo in cultured cells. *The Journal of cell biology* 132: 643-655.
Goulielmos, G., S. Remington, F. Schwesinger, S. D. Georgatos, and F. Gounari. 1996. Contributions of the structural domains of filensin in polymer formation and filament distribution. *Journal of cell science* 109 ( Pt 2): 447-456.
Green DR & Reed JC. 1998. Mitochondria and apoptosis. Science 281(5381):1309-12.
Gruzman, A., A. Hidmi, J. Katzhendler, A. Haj-Yehie, and S. Sasson. 2004. Synthesis and characterization of new and potent alpha-lipoic acid derivatives. *Bioorganic & medicinal chemistry* 12: 1183-1190.
Guest, P. C., H. A. Skynner, K. Salim, F. D. Tattersall, M. R. Knowles, and J. R. Atack. 2006. Detection of gender differences in rat lens proteins using 2-D-DIGE. *Proteomics* 6: 667-676.
Gurney AM. 1994. Flash photolysis of caged compounds in *Microelectrode Techniques*, ed Ogden D, pp. 389-406.
Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.
Hardie RC. 1995. Photolysis of Caged $Ca^{2+}$ Facilitates and inactivates but Does Not Directly Excite Light-Sensitive Channels in *Drosophila* Photoreceptors. J Neurosci 15(1):899-902.
Heidemann, S. R., S. Kaech, R. E. Buxbaum, and A. Matus. 1999. Direct observations of the mechanical behaviors of the cytoskeleton in living fibroblasts. *The Journal of cell biology* 145: 109-122.
Hermans, E., M. Dubbelman, R. van der Heijde, and R. Heethaar. 2007. The shape of the human lens nucleus with accommodation. *Journal of vision* 7: 16 11-10.
Hofmann, M., P. Mainka, H. Tritschler, J. Fuchs, and G. Zimmer. 1995. Decrease of red cell membrane fluidity and—SH groups due to hyperglycemic conditions is counteracted by alpha-lipoic acid. *Archives of biochemistry and biophysics* 324: 85-92.
Hung CC, et al. 2003. Protection of renal epithelial cells against oxidative injury by endoplasmic reticulum stress preconditioning is mediated by ERK1/2 activation. J Biol Chem. 278(31):29317-26. Epub May 8, 2003.
Ip C, Ganther HE. 1992. Comparison of selenium and sulfur analogs in cancer prevention. Carcinogenesis. 13(7): 1167-70.
Ivanov, D., G. Dvoriantchikova, A. Pestova, L. Nathanson, and V. I. Shestopalov. 2005. Microarray analysis of fiber cell maturation in the lens. *FEBS letters* 579: 1213-1219.
Janoria, K. G., S. Hariharan, D. Paturi, D. Pal, and A. K. Mitra. 2006. Biotin uptake by rabbit corneal epithelial cells: role of sodium-dependent multivitamin transporter (SMVT). *Current eye research* 31: 797-809.
Jimenez-Orozco, F. A., J. S. Lopez-Gonzalez, A. Nieto-Rodriguez, M. A. Velasco-Velazquez, J. A. Molina-Guarneros, N. Mendoza-Patino, M. J. Garcia-Mondragon, P. Elizalde-Galvan, F. Leon-Cedeno, and J. J. Mandoki. 2001. Decrease of cyclin D1 in the human lung adenocarcinoma cell line A-427 by 7-hydroxycoumarin. *Lung cancer* (Amsterdam, Netherlands) 34: 185-194.

Johansson, M., and M. Lundberg. 2007. Glutathionylation of beta-actin via a cysteinyl sulfenic acid intermediary. *BMC Biochem* 8: 26.

Jones, D. P., Y. M. Go, C. L. Anderson, T. R. Ziegler, J. M. Kinkade, Jr., and W. G. Kirlin. 2004. Cysteine/cystine couple is a newly recognized node in the circuitry for biologic redox signaling and control. *Faseb J* 18: 1246-1248.

Jung MY, et al. 2001. Chemopreventive allylthiopyridazine derivatives induce apoptosis in SK-Hep-1 hepatocarcinoma cells through a caspase-3-dependent mechanism. Eur J Cancer. 37(16):2104-10.

Jürgen W. 2007. Synthesis and investigations of (6-hydroxy-3-oxo-3H-xanthen-9-yl)methyl derivatives. A new photoremovable protecting group. Inaugural Dissertation at Universität Basel.

Kahn, J., P. Preis, F. Waldman, and A. Tseng, Jr. 1994. Coumarin modulates the cell-cycle progression of an MTV-EJras cell line. *Journal of cancer research and clinical oncology* 120 Suppl: S19-22.

Kao, JPY. 2006. Caged molecules: principles and practical considerations. Curr Protoc Neurosci 6.20.1-6.20.21.

Kibbelaar, M. A., F. C. Ramaekers, P. J. Ringens, A. M. Selten-Versteegen, L. G. Poels, P. H. Jap, A. L. van Rossum, T. E. Feltkamp, and H. Bloemendal. 1980. Is actin in eye lens a possible factor in visual accomodation? *Nature* 285: 506-508.

Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.

Konrad, D., R. Somwar, G. Sweeney, K. Yaworsky, M. Hayashi, T. Ramlal, and A. Klip. 2001. The antihyperglycemic drug alpha-lipoic acid stimulates glucose uptake via both GLUT4 translocation and GLUT4 activation: potential role of p38 mitogen-activated protein kinase in GLUT4 activation. *Diabetes* 50: 1464-1471.

Kumar RV, et al. 1991. The nature of inhibition of 3-hydroxy-3-methylglutaryl CoA reductase by garlic-derived diallyl disulfide. Biochim Biophys Acta. 1078(2):219-25.

Kuszak, J. R., A. R. Khan, and R. J. Cenedella. 1988. An ultrastructural analysis of plasma membrane in the U18666A cataract. *Investigative ophthalmology & visual science* 29: 261-267.

Lacy, A., and R. O'Kennedy, 2004. Studies on coumarins and coumarin-related compounds to determine their therapeutic role in the treatment of cancer. *Current pharmaceutical design* 10: 3797-3811.

Larsson, H. P., A. V. Tzingounis, H. P. Koch, and M. P. Kavanaugh. 2004. Fluorometric measurements of conformational changes in glutamate transporters. *Proceedings of the National Academy of Sciences of the United States of America* 101: 3951-3956.

Lesiński L & Duschmalé J. 2006. Flash Photolysis in Praktikum "Physikalische Chemie," pp. 1-8.

Li, L., J. Lim, M. D. Jacobs, J. Kistler, and P. J. Donaldson. 2007. Regional differences in cystine accumulation point to a sutural delivery pathway to the lens core. *Investigative ophthalmology & visual science* 48: 1253-1260.

Li, X., Liu, Z., et al. 2008. Lipoamide protects retinal pigment epithelial cells from oxidative stress and mitochondrial dysfunction. *Free Radic Biol Med.* 44(7): 1465-1474.

Lim, J., Y. C. Lam, J. Kistler, and P. J. Donaldson. 2005. Molecular characterization of the cystine/glutamate exchanger and the excitatory amino acid transporters in the rat lens. *Investigative ophthalmology & visual science* 46: 2869-2877.

Lim, J., L. Li, M. D. Jacobs, J. Kistler, and P. J. Donaldson. 2007. mapping of the glutathione and its precursor amino acids reveals a role for GLYT2 in glycine uptake in the lens core. *Investigative ophthalmology & visual science* 48: 5142-5151.

Lindsey Rose, K. M., R. G. Gourdie, A. R. Prescott, R. A. Quinlan, R. K. Crouch, and K. L. Schey. 2006. The C terminus of lens aquaporin 0 interacts with the cytoskeletal proteins filensin and CP49. *Investigative ophthalmology & visual science* 47: 1562-1570.

Liu H, et al. 1997. Endoplasmic reticulum chaperones GRP78 and calreticulin prevent oxidative stress, Ca2+ disturbances, and cell death in renal epithelial cells. J Biol Chem. 272(35):21751-9.

Liu, J., E. Head, A. A. Gharib, W. Yuan, R. T. Ingersoll, T. M. Hagen, C. W. Cotman, and B. N. Ames. 2002. Memory loss in old rats is associated with brian mitochondrial decay and RNA/DNA oxidation: Partial reversal by feeding acetyl-L-carnitine and/or R-alpha-lipoic acid. *Proceedings of the National Academy of Sciences of the United States of America* 99: 2356-2361.

Lopez-Gonzalez, J. S., H. Prado-Garcia, D. Aguilar-Cazares, J. A. Molina-Guarneros, J. Morales-Fuentes, and J. J. Mandoki. 2004. Apoptosis and cell cycle disturbances induced by coumarin and 7-hydroxycoumarin on human lung carcinoma cell lines. *Lung cancer* (Amsterdam, Netherlands) 43: 275-283.

Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. *Mol Pharm* 3: 329-339.

Maitra, I., E. Serbinova, H. J. Tritschler, and L. Packer. 1996. Stereospecific effects of R-lipoic acid on buthionine sulfoximine-induced cataract formation in newborn rats. *Biochemical and biophysical research communications* 221: 422-429.

Maitra, I., E. Serbinova, H. Trischler, and L. Packer. 1995. Alpha-lipoic acid prevents buthionine sulfoximine-induced cataract formation in newborn rats. *Free radical biology & medicine* 18: 823-829.

Manns, F., J. M. Parel, D. Denham, C. Billotte, N. Ziebarth, D. Borja, V. Fernandez, M. Aly, E. Arrieta, A. Ho, and B. Holden. 2007. Optomechanical response of human and monkey lenses in a lens stretcher. *Investigative ophthalmology & visual science* 48: 3260-3268.

Merdes, A., M. Brunkener, H. Horstmann, and S. D. Georgatos. 1991. Filensin: a new vimentin-binding, polymerization-competent, and membrane-associated protein of the lens fiber cell. *The Journal of cell biology* 115: 397-410.

Merdes, A., F. Gounari, and S. D. Georgatos. 1993. The 47-kD lens-specific protein phakinin is a tailless intermediate filament protein and an assembly partner of filensin. *The Journal of cell biology* 123: 1507-1516.

Moini, H., O. Tirosh, Y. C. Park, K. J. Cho, and L. Packer. 2002. R-alpha-lipoic acid action on cell redox status, the insulin receptor, and glucose uptake in 3T3-L1 adipocytes. *Archives of biochemistry and biophysics* 397: 384-391.

Muchowski, P. J., M. M. Valdez, and J. I. Clark. 1999. AlphaB-crystallin selectively targets intermediate filament proteins during thermal stress. *Investigative ophthalmology & visual science* 40: 951-958.

Musk SR, et al. 1997. Cytotoxicity and genotoxicity of diallyl sulfide and diallyl disulfide towards Chinese hamster ovary cells. Food Chem Toxicol. 35(3-4):379-85.

Obrosova I, et al. 1998. Diabetes-induced changes in lens antioxidant status, glucose utilization and energy metabolism: effect of DL-alpha-lipoic acid. Diabetologia 41(12):1442-50.

Ong, M. D., D. M. Payne, and M. H. Garner. 2003. Differential protein expression in lens epithelial whole-mounts and lens epithelial cell cultures. *Experimental eye research* 77: 35-49.

Pau, H., and J. Kranz. 1991. The increasing sclerosis of the human lens with age and its relevance to accommodation and presbyopia. *Graefe's archive for clinical and experimental ophthalmology=Albrecht von Graefes Archiv fur klinische and experimentelle Ophthalmologie* 229: 294-296.

Petit PX, et al. 1995. Alterations in mitochondrial structure and function are early events of dexamethasone-induced thymocyte apoptosis. J Cell Biol. 130(1):157-67.

Pierscionek, B. K. 1995. Age-related response of human lenses to stretching forces. *Experimental eye research* 60: 325-332.

Reddy, N. S., K. Gumireddy, M. R. Mallireddigari, S. C. Cosenza, P. Venkatapuram, S. C. Bell, E. P. Reddy, and M. V. Reddy. 2005. Novel coumarin-3-(N-aryl)carboxamides arrest breast cancer cell growth by inhibiting ErbB-2 and ERK1. *Bioorganic & medicinal chemistry* 13: 3141-3147.

Salvioli S, et al. 1997. JC-1, but not DiOC6(3) or rhodamine 123, is a reliable fluorescent probe to assess delta psi changes in intact cells: implications for studies on mitochondrial functionality during apoptosis. FEBS Lett. 411(1):77-82.

Sandilands, A., A. R. Prescott, A. M. Hutcheson, R. A. Quinlan, J. T. Casselman, and P. G. FitzGerald. 1995. Filensin is proteolytically processed during lens fiber cell differentiation by multiple independent pathways. *European journal of cell biology* 67: 238-253.

Sato, H., M. Tamba, K. Kuriyama-Matsumura, S. Okuno, and S. Bannai. 2000. Molecular cloning and expression of human xCT, the light chain of amino acid transport system xc. *Antioxid Redox Signal* 2: 665-671.

Sato, H., M. Tamba, T. Ishii, and S. Bannai. 1999. Cloning and expression of a plasma membrane cystine/glutamate exchange transporter composed of two distinct proteins. *The Journal of biological chemistry* 274: 11455-11458.

Sato, H., A. Shiiya, M. Kimata, K. Maebara, M. Tamba, Y. Sakakura, N. Makino, F. Sugiyama, K. Yagami, T. Moriguchi, S. Takahashi, and S. Bannai. 2005. Redox imbalance in cystine/glutamate transporter-deficient mice. *The Journal of biological chemistry* 280: 37423-37429.

Schonheit, K., L. Gille, and H. Nohl. 1995. Effect of alpha-lipoic acid and dihydrolipoic acid on ischemia/reperfusion injury of the heart and heart mitochondria. *Biochimica et biophysica acta* 1271: 335-342.

Senda N. et al. 2006. Synthesis and Photochemical Properties of a New Water-Soluble Coumarin, Designed as a Chromophore for Highly Water-Soluble and Photolabile Protecting Group. Bull. Chem. Soc. Jpn. 79(11): 1753-1757.

Shembekar, V. R., Y. Chen, B. K. Carpenter, and G. P. Hess. 2005. A protecting group for carboxylic acids that can be photolyzed by visible light. *Biochemistry* 44: 7107-7114.

Strenk, S. A., L. M. Strenk, J. L. Semmlow, and J. K. DeMarco. 2004. Magnetic resonance imaging study of the effects of age and accommodation on the human lens cross-sectional area. *Investigative ophthalmology & visual science* 45: 539-545.

Sundaram SG & Milner JA. 1996. Diallyl disulfide suppresses the growth of human colon tumor cell xenografts in athymic nude mice. J Nutr. 126(5):1355-61.

Sweeney, M. H., and R. J. Truscott. 1998. An impediment to glutathione diffusion in older normal human lenses: a possible precondition for nuclear cataract. *Experimental eye research* 67: 587-595.

Tamm, E., E. Lutjen-Drecoll, W. Jungkunz, and J. W. Rohen. 1991. Posterior attachment of ciliary muscle in young, accommodating old, presbyopic monkeys. *Investigative ophthalmology & visual science* 32: 1678-1692.

Tamm, S., E. Tamm, and J. W. Rohen. 1992. Age-related changes of the human ciliary muscle. A quantitative morphometric study. *Mechanisms of ageing and development* 62: 209-221.

Trayhurn P. and Van Heyningen R. 1973. The Metabolism of Amino Acids in the Bovine Lens; Their Oxidation as a Source of Energy. *Biochem. J.* 136:67-75.

Truscott, R. J. 2000. Age-related nuclear cataract: a lens transport problem. *Ophthalmic research* 32: 185-194.

Wakabayashi, Y. et al. 2006. Glutamate Levels in Aqueous Humor of Patients with Retinal Artery Occlusion. *Retina* 26:432-436.

Wang, C. J., Y. J. Hsieh, C. Y. Chu, Y. L. Lin, and T. H. Tseng. 2002. Inhibition of cell cycle progression in human leukemia HL-60 cells by esculetin. *Cancer letters* 183: 163-168.

Wang, S. J., and H. H. Chen. 2007. Presynaptic mechanisms underlying the alpha-lipoic acid facilitation of glutamate exocytosis in rat cerebral cortex nerve terminals. *Neurochemistry international* 50: 51-60.

Weeber, HA et al. 2007. Stiffness gradient in the crystalline lens. Graefes Arch Clin Exp Ophthalmol 245(9):1357-66.

Widomska, J., M. Raguz, J. Dillon, E. R. Gaillard, and W. K. Subczynski. 2007. Physical properties of the lipid bilayer membrane made of calf lens lipids: EPR spin labeling studies. *Biochimica et biophysica acta* 1768: 1454-1465.

Wieboldt R et al. 1994. Photolabile precursors of glutamate: Synthesis, photochemical properties, and activation of glutamate receptors on a microsecond time scale. Proc. Natl. Acad. Sci. 91:8752-8756.

Yin MC, et al. 2002. Nonenzymatic antioxidant activity of four organosulfur compounds derived from garlic. J Agric Food Chem. 50(21):6143-7.

Yu, N. T., D. C. DeNagel, P. L. Pruett, and J. F. Kuck, Jr. 1985. Disulfide bond formation in the eye lens. *Proceedings of the National Academy of Sciences of the United States of America* 82: 7965-7968.

Zhao, Y., Q. Zheng, K. Dakin, K. Xu, M. L. Martinez, and W. H. Li. 2004. New caged coumarin fluorophores with extraordinary uncaging cross sections suitable for biological imaging applications. *Journal of the American Chemical Society* 126: 4653-4663.

Zivkovic, D. 2007. Investigations on 2,7-diamino-9-fluorenol photochemistry. Inaugural Dissertation at Universität Basel.

Zwingmann, C. et al. 2001. $^{13}$C Isotopomer Analysis of Glucose and Alanine Metabolism Reveals Cytosolic Pyruvate Compartmentation as Part of Energy Metabolism in Astrocytes. *GLIA* 34:200-212.

Aloisi et al. 1948. Glycerylphosphorylcholine and Choline Glycerophosphate. Biochemical Journal. vol. 43, pp. 157-161; p. 157, col. 1, para 2-3; col. 2, para 1; p. 158, col. 1, para 4.

Gilbert, Basic Concepts in Biochemistry USA. McGraw Hill 2000 p. 184.

Jablonski et al. Plant Physiology 1978 61:221-225.

Ng et al. Experimental Eye Research 1986 43:477-489.

JP Office Action in JP2007-537922.

PRESBYOPIA TREATMENT BY LENS ALTERATION

CROSS-REFERENCES TO RELATED APPLICATIONS

This application is a continuation-in-part of U.S. patent application Ser. No. 11/135,271 filed May 24, 2005 (which claims priority to U.S. Provisional Application 60/574,211 filed May 26, 2004), U.S. patent application Ser. No. 11/010,436 filed Dec. 14, 2004, and U.S. patent application Ser. No. 10/969,868 filed Oct. 22, 2004, each of which is a continuation or continuation-in-part of U.S. patent application Ser. No. 10/050,879 filed Jan. 18, 2002, now U.S. Pat. No. 6,923,955, which claims priority to U.S. Provisional Application 60/262,423 filed Jan. 19, 2001, and is a continuation-in-part of U.S. patent application Ser. No. 09/930,287 filed Aug. 16, 2001, now abandoned, which claims priority to U.S. Provisional Application 60/225,659 filed Aug. 16, 2000. This application also claims priority to U.S. Provisional Applications 60/861,262 filed Nov. 28, 2006; 60/907,734 filed Apr. 16, 2007; and 60/924,686 filed May 29, 2007.

FIELD OF THE INVENTION

The present invention relates to methods, devices, and agents for preventing, reversing, and/or treating presbyopia.

BACKGROUND OF THE INVENTION

Presbyopia affects virtually every person over the age of 44. According to Jobson Optical Database, 93% of people 45 and over are presbyopic. Today there are an estimated 1.6 billion humans on earth (of which approximately 100 million are in the USA) that are presbyopic, and the number is growing. Presbyopia entails the progressive loss of amplitude of accommodation that occurs with aging. Adler's Physiology of the Eye, which is incorporated herein by reference, discloses that the human accommodative amplitude declines with age such that accommodation is substantially eliminated by the age of 50 to 55. Accommodative ability, as defined by U.S. Pat. No. 5,459,133 to Neufeld and incorporated in its entirety herein by reference for background information, is the capacity of the eye to focus for near vision by changing the shape of the lens to become more convex.

The ocular tissues involved in the accommodative response include the lens (e.g., the crystalline lens), the zonules, the lens capsule, and the ciliary muscle. Of these, the lens is the central tissue. These structures function together to enable the eye to focus on close objects by changing the shape of the lens. The lens is centrally suspended between the anterior and posterior chambers behind the pupillary opening of the iris. The lens is supported by an array of radially oriented zonular fibers, which extend from the lateral edges of the lens to the inner border of the circumferential ciliary muscle. The ciliary muscle is attached to the scleral coat of the eye. When the eye is at rest, it is focused for distance, and the lens is in a somewhat flattened or less convex position. This shape is due to the tension that is exerted on the lens periphery by the zonules. The zonules pull the edges of the lens toward the ciliary body.

During accommodation, the shape of the anterior surface of the lens becomes more convex through contraction of the ciliary muscle, which allows the ciliary attachment of the zonules to move toward the lens, reducing the tension in the anterior zonules. This reduction in tension allows the central region of the lens to increase in convexity, thereby enabling near objects to be imaged on the retina. The processes involving the coordinated effort of the lens, zonules, ciliary body, medial rectus muscles, and iris, among others, that lead to the ability of the eyes to clearly focus near on the retina is the accommodative process.

Several theories have been advanced to explain the loss of accommodation with age. These theories include the hardening of the lens with age, loss of strength in the ciliary muscle, factors related to the physical growth of the lens, and the loss of elasticity of the lens capsule. As for the loss of strength of the ciliary muscle, it is noted that although there are age-related morphological changes that occur, there is little evidence of diminishing strength of the ciliary muscle. In fact, under the influence of pilocarpine, the ciliary muscle will vigorously contract even in presbyopic eyes.

The lens grows throughout one's life, and theories have been proposed that it is this increase in size that prohibits the effects of the zonules from affecting a change in the shape of the lens. Recent works exploring this possibility have not met widespread acceptance thus far. Most of the growth of the lens is not in its diameter, but instead, in its anterior-posterior dimensions.

As for changes in the lens capsule, it has been postulated that reduction in the elasticity of the capsule is, in fact, a contributing factor in presbyopia. Moreover, it has been found that Young's modulus of elasticity for the lens capsule decreases by nearly 50% from youth to age 60, while accommodation decreases by 98%. Consequently, the principal cause of presbyopia is now considered to be "lenticular sclerosis" or the hardening of the lens.

A cataract is a condition in which the lens becomes less clear. The study of cataracts lends insight into lens and capsular changes. The usual senile cataract is relatively discus-shaped when removed from the eye, its shape being dictated by the firm lens substance. The liquefied hypermature cataract is globular when extracted, rounded up by the elastic lens capsule. This is indirect evidence that it may be possible to reverse the lenticular changes associated with presbyopia, and that the lens capsule is still sufficiently elastic.

At the present time, common device treatments for presbyopia include reading glasses, bifocal glasses, mono-vision contact lenses, multifocal intra-ocular lenses, accommodating intra-ocular lenses, and corneal inlays. All of these solutions necessitate the use of an appliance creating additional shortcomings.

Alternative theories and procedures for treating presbyopia include scleral expansion and corneal reshaping. The efficacy of such techniques is not well-established, and importantly, these techniques do not attempt to reverse what the inventors of the subject-application believe to be a substantial causation, as explained more fully below, in the loss of the accommodative amplitude of the lens typically associated with the normal aging process. Moreover, because scleral expansion and corneal reshaping involve macroscopic changes in the morphology of the lens and/or cornea, it fails to reverse presbyopia.

Finally, the use of the excimer laser for the purposes of corneal reshaping to produce a multifocal refracting surface has been disclosed in U.S. Pat. No. 5,395,356. While this method seems promising, it still requires structural changes to the cornea to compensate for aging changes in the lens. Rather than trying to undo the changes brought on by presbyopia, techniques such as these merely compensate for the loss of accommodative function by altering another ocular structure.

BRIEF SUMMARY OF THE INVENTION

While not wishing to be bound to any particular theory, the inventors believe that presbyopia is caused by the hardening of the lens, which can be due to an alteration of the structural proteins or an increased adhesion between the lens fibers. It is also believed that the intralenticular viscosity increases with age as a result of the formation of certain chemical bond structures within the lens. Accordingly, the present invention is directed to methods, devices, and agents for preventing and/or reversing presbyopia through treatment of the lens such that the viscosity or stiffness of the lens is reduced, restoring the elasticity and movement to the lens fibers and increasing the accommodative amplitude of the lens.

The claimed invention is also directed to a method of preventing, reversing, and/or treating presbyopia resulting in underlying changes in the structures and/or interactions of molecules comprising those components of the eye associated with the accommodative process, most notably the lens and/or lens capsule. The net result will be to increase the accommodative ability of the eye or eyes provided the inventive method/treatment.

In an embodiment, the present invention provides a novel molecular approach to preventing and/or reversing presbyopia by restoring the accommodative amplitude of the lens, and in another preferred embodiment, to reversing presbyopia while also reducing the tendency for the lens to lose its thus restored accommodative amplitude.

In another embodiment of the invention, the onset of presbyopia is prevented by regularly administered treatment where elasticity and the accommodative ability of the lens is restored. By applying the treatments as described herein to the eyes of persons in their mid- to late 30's, or even younger, the onset of presbyopia, as defined by a loss of accommodation, such that the accommodative power of the eye is below 2.5 Diopters, can be avoided. In one embodiment of the invention, such treatments, whether for the purposes of preventing or reversing presbyopia, would be occasionally repeated during the course of a patient's lifetime. The frequency of the treatment would be determined by the degree of accommodative loss that needs to be recovered, the amount of accommodation that can be safely restored in a single procedure, and the amount of restoration desired.

In one embodiment, the present invention is directed to a method for reversing and/or treating presbyopia by breaking disulfide bonds in molecules comprising the structures of the eye, most notably the lens and the lens capsule, in which disulfide bonds are believed to be a substantial factor in the progressive loss of accommodative amplitude. In another embodiment, the breaking of the disulfide bonds is accompanied by chemical modification of the sulfur moiety in the cysteine molecule formed upon breaking of the disulfide bonds, such chemical modification rendering the sulfur moiety less likely to form new disulfide bonds. This method thus comprises a method for preventing and/or reducing the recurrence of presbyopia by reducing the probability of forming new disulfide bonds. Particularly, this invention effects a change in the accommodative amplitude of the human lens by: (1) using various reducing agents that can a change in the accommodative abilities of the human lens, and/or (2) the use of applied energy to effect a change in the accommodative abilities of the human lens. The inventors have determined that by breaking bonds, such as disulfides, that crosslink lens fibers together and increase lens viscosity causing a hardening of the lens cortex and lens nucleus, it is possible to increase the elasticity and the distendsibility of the lens cortex, lens nucleus, and/or the lens capsule without causing substantial damage to the living lens fibers and tissues. In one embodiment, the method increases accommodative amplitude while maintaining one or more optical properties of the lens, e.g., lens transparency and optical power.

Presbyopia, or the loss of the accommodative amplitude of the lens, has often advanced in a typical person age 45 or older to the point where some type of corrective lens in the form of reading glasses or other treatment is required. It is to be understood that loss of accommodative amplitude can occur in persons much younger or older than the age of 45, thus the present invention is not to be construed as limited to the treatment of presbyopia in a person of any particular age. The present invention is most useful in a person whose accommodative amplitude has lessened to a point where restoration thereof to some degree is desirable. However the invention should not be limited to the correction of presbyopia, but may be used to prevent presbyopia from occurring.

In one embodiment, the method increases accommodative amplitude by at least about +0.12 D, about +0.25 D, about +0.5 D, about +0.75 D, about +1.00 D, about +1.25 D, about +1.5 D, about +1.8 D, about +2.0 D, about +2.5 D, or about +5.0 D. In one embodiment of the present invention, the method of reversing or preventing presbyopia will result in an increase in the accommodative amplitude at least about by 0.5 diopters. In another embodiment of the present invention, the method of reversing or preventing presbyopia will result in an increase in the accommodative amplitude of at least about 2.0 diopters. In still another embodiment, the method of reversing or preventing presbyopia of the present invention will result in an increase in the accommodative amplitude by at least about 5 diopters. In another embodiment of the present invention, the method of reversing or preventing presbyopia of the present invention will result in an increase of the accommodative amplitude of the lens to restoration thereof to that of a lens with a normal accommodative amplitude of 2.5 diopters or greater.

It is noted that while it is obviously most beneficial to restore the accommodative amplitude of the lens to a normal accommodative amplitude, lesser degrees of restoration are also beneficial. For example, in some cases, advanced presbyopia can cause severe reduction in the accommodative amplitude, thus making a complete restoration of the amplitude improbable.

DETAILED DESCRIPTION OF THE INVENTION

Figure 1:
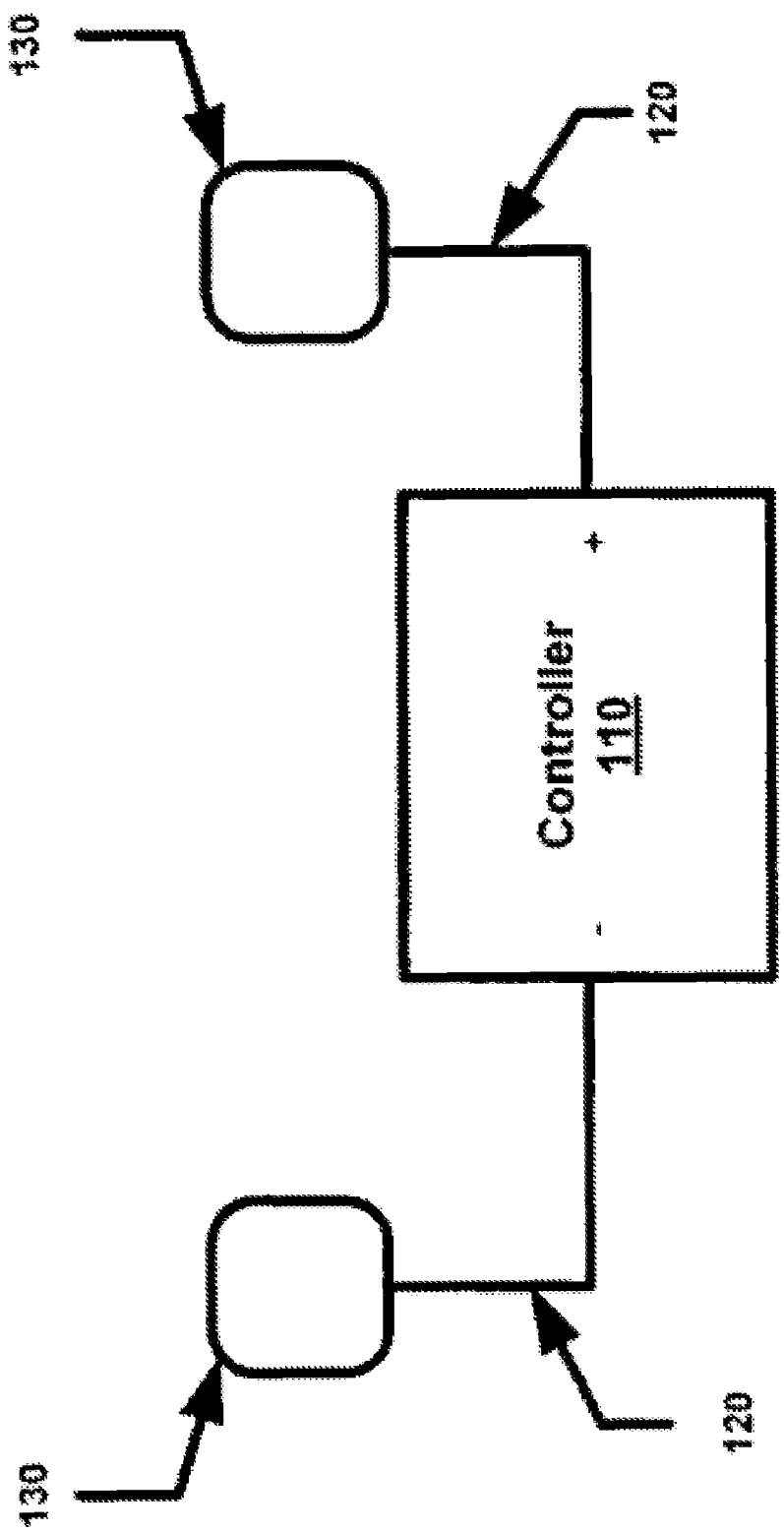
FIG. 1 illustrates an iontophoretic device that may be used with methods according to embodiments of the present invention.

The accommodative amplitude of the lens is measured in diopters (D). The loss of accommodative ability begins at a very early age, such that by age 10 the average eye has 10 D, age 30, 5 D, and by age 40, only 2.5 D of accommodative power. The lens of a person who does not suffer from presbyopia (i.e., a person whose lens accommodates normally) will typically have an accommodative amplitude of about 2.5 diopters or greater. The terms "preventing presbyopia," "reversing presbyopia," or "treating presbyopia" as used herein mean increasing the accommodative amplitude of the lens. "Preventing presbyopia" also includes maintaining a normal level of accommodative amplitude and/or preventing or slowing the loss of accommodative amplitude.

As stated, inelasticity of the lens, or hardening thereof, is believed to be a contributing cause of presbyopia. The hardening of the lens can be due to an alteration of the structural proteins or an increased adhesion between the lens fibers. This can be caused by the formation of protein-to-protein bonds, specifically, disulfide bonds. Additionally, the inventors believe that the lens viscosity also increases with age due to an increased concentration of certain chemical bond structures within the lens. In one embodiment, the present invention is directed to treating presbyopia by altering the molecular and/or cellular bonds between the cortical lens fibers so as to free their movement with respect to each other. The increased elasticity of the lens apparatus can restore lost amplitude of accommodation. Specifically, the inventors have proven that disulfide bonds in the molecules comprising the structures of the eye responsible for proper accommodation are a substantial factor in the hardening of the lens and the concomitant loss of accommodative amplitude.

Thus, one embodiment of the invention involves breaking the disulfide bond and then protonating the newly formed sulfur moiety with a reducing agent such as glutathione to impart a hydrogen atom thereto. The steps can be performed simultaneously or consecutively. In either case, the reducing agent can be present at the time the disulfide bond is broken in order to eliminate reformation of disulfide. That is, the reducing agent can introduce and bond a moiety onto the free sulfur after breaking the disulfide bond such that the likelihood of reformation of another disulfide bond is prevented or at least reduced. While the reducing agent may introduce a hydrogen atom onto the free sulfur, thus forming a sulfhydryl group (—SH), the resultant —SH groups can again be oxidized to form a new disulfide bond. Thus, it is advantageous to introduce a group into the free sulfur moiety, such as lower alkyls, methylating compounds, or other agents, which reduce the tendency of new disulfide bond formation. This method can result in a substantial prevention of the reoccurrence of presbyopia.

As stated, the inventors believe that unwanted disulfide bonds form both between the lens fibers, between lens proteins, and between lens proteins and various thiols both within and on lens fibers. These bonds can substantially reduce the lens fibers' ability to easily move relative to each other and thus the ability of the lens to accommodate properly. While not wishing to be bound by any particular chemical mode that causes the bonds to first form, the bonds may form by way of example only, by the absorption of light energy, which causes the sulfhydryl bonds on the lens proteins to oxygenate removing a hydrogen atom from two adjacent —SH groups and creating water and a disulfide bond. Other oxidizing agents include, but are not limited to, ultraviolet light, nitrites, nitrous oxide, superoxides, or other known or yet to be discovered oxidizing agents. Reducing the disulfide bonds, which may require hydrogen donors such as glutathione or other molecules, is the fundamental methodology employed by the invention. It is believed the experiment and results being disclosed herein prove that by breaking these unwanted disulfide bonds and their reduction, it is possible to increase the accommodative amplitude. Other possible theories involve protein-thiol mixed disulfide bonds forming such as protein-S—S-glutathione or protein-S—S-cysteine. Glutathione therefore may be both part of the solution and part of the problem. The use of glutathione in any treatment regimen therefore must be monitored carefully in light of the potential for an increase in undesirable bond formation.

The total refractive power of the lens is greater than what would be expected based on the curvature and the index of refraction. As stated, contraction of the ciliary muscle causes the ciliary body to move forward and towards the equator of the lens. This causes the zonules to relax their tension on the lens capsule, which allows the central lens to assume a more spherical shape. During accommodation, the main change is in the more central radius of curvature of the anterior lens surface, which is 12 mm in the unaccommodative state and can be 3 mm centrally during accommodation. Both the peripheral anterior and the posterior lens surfaces change very little in curvature during accommodation. The axial thickness increases while the diameter decreases. The central anterior lens capsule is thinner than the rest of the anterior capsule. This may explain why the lens bulges more centrally during accommodation. The thinnest portion of the capsule is the posterior capsule, which has a curvature greater than the anterior capsule in the unaccommodative state. The protein content of the lens, almost 33% by weight, is higher than any other organ in the body.

There are many chemical compounds of special interest in the lens. For example, glutathione is found in high concentration in the lens cortex even though there is very little in the aqueous. Thus, the lens has a great affinity for glutathione and actively absorbs, transports and synthesizes glutathione. Approximately 93% of intralenticular glutathione is in the reduced form. Glutathione may be involved with maintaining the lens proteins, the sulfhydryl groups (—SH), in their reduced states. That is, after the disulfide bond is broken and the sulfur moieties are made available, glutathione can impart a hydrogen atom to form the sulfhydryl group thereby preventing or minimizing the reformation of a disulfide bond. In addition, ascorbic acid can also be found in very high concentrations in the lens. It is actively transported out of the aqueous and is at concentrations 15 times that found in the bloodstream. Both inositol and taurine are found at high concentrations in the lens for which the reason is not known.

According to one embodiment of the invention, the increase in the accommodative amplitude is accomplished by treatment of the outer lens region (the cortex) or the inner layer (the nucleus) with radiation, sonic or electromagnetic energy, heat, chemical, particle beam, plasma beam, enzyme, gene therapy, nutrients, other applied energy source, and/or any combination of any of the above sufficient to break the disulfide bonds believed responsible for the inelasticity of the lens. Chemicals are useful to reduce disulfide bonds that are believed to anchor lens fibers hence preventing their free movement and elasticity. By making the anterior cortex and/or the nucleus more elastic, viscosity is lowered, and the lens is again able to assume its characteristic central bulge during accommodation.

Chemicals suitable for causing reduction include, by way of example only, glutathione, ascorbic acid, Vitamin E, tetraethylthiuram disulfyl, i.e., reducing agent, any biologically suitable easily oxidized compound, ophthalmic acid, inositol, beta-carbolines, any biologically suitable reducing compound, reducing thiol derivatives with the structure:

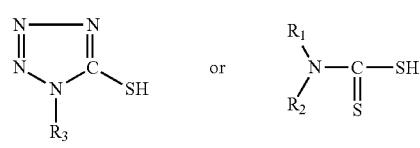

or sulfur derivatives with the structures:

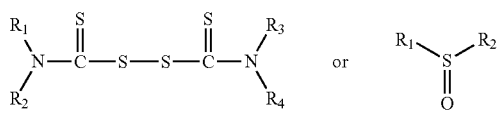

Wherein $R_1$, $R_2$, $R_3$, and $R_4$ are independently a straight or branched lower alkyl that may be substituted, e.g., by hydroxyl, lower alkoxy, or lower alkyl carbonyloxy, their derivatives or a pharmaceutically acceptable salt thereof. Preferred exemplary reducing agents include diethyl dithiocarbamate, 1-methyl-1H-tetrazol-5-yl-thiol and 1-(2-hydroxyethyl)-1H-tetrazol-5-yl-thiol or and pharmaceutically acceptable salts thereof. Other useful compounds can be found in U.S. Pat. No. 5,874,455, which is hereby incorporated in its entirety by reference for background information.

Other chemicals suitable for causing reduction include, but are not limited to, thiodisulfide exchange reaction agents such as dithiothreitol (DTT, Cleland's reagent, having the structure HS—$CH_2$—CHOH—CHOH—$CH_2$—SH), trialkylphosphine, and tris[2-carboxyethyl]phosphine hydrochloride (TCEP.HCl). In one embodiment, the chemical is DTT. Chemicals can also include, but are not limited to, naturally occurring enzymes such as thioredoxin. In one embodiment, the chemical is thioredoxin.

The above-mentioned chemicals are merely exemplary and other reducing agents that behave similarly by breaking the disulfide bond are included within the scope of this invention.

One embodiment of the invention involves breaking and reducing the disulfide bond with threo-1,4-dimercapto-2,3,butane-diol, also known as dithiothreitol (DTT) or Cleland's Reagent. The invention further contemplates the use of a similar agent or derivative of DTT. In Example 1, the lens appeared to naturally (without any external aid) take on its naturally relaxed mostly spherical shape showing an increase in its anterior curvature as the DTT broke and reduced the unwanted disulfide bonds. Example 1 demonstrated without question the ability to soften the lens with the use of DTT.

While most biologically acceptable pharmaceutical agents will need to work in combination with an energy source, some agents such as DTT can both break and reduce unwanted disulfide bonds through a chemical reaction and do not require externally applied energy. Thus, when a more aggressive agent is used, e.g., one that can act via a strictly chemical reaction, externally applied energy may not be required. In other words, the more aggressive the reducing agent, the less (or none at all) externally applied energy is required; the weaker the reducing agent (e.g., the less redox potential), the more externally applied energy is required. One of ordinary skill in the art can identify when an agent's action is a strictly chemical reaction and can select the appropriate balance between redox potential and externally applied energy.

According to one embodiment of the invention, the increase in the accommodative amplitude is accomplished by treatment of the outer lens region (the cortex) or the inner layer (the nucleus) with thioredoxin.

The chemical reducing agents can be used alone or in conjunction with a catalyst such as an enzyme. Enzymes and other nutrients suitable for causing or facilitating reduction include, for example, aldoreductase, glyoxylase, glutathione S-transferase, hexokinase, thiol reductase, thioltransferase, tyrosine reductase, thioredoxin reductase, or any compatible reductase. The need for a source of applied energy for the reduction of the disulfide bonds may be met by the nature of the reducing agent such as dithiothreitol (DTT), which chemically is able to reduce disulfide bonds, or be met by the addition of glucose-6-phosphate, which is present within the lens but the enzyme, hexokinase that normally converts the glucose to the G6P energy state is rendered non-functional by the process of thiol oxidation, or any other chemical or externally applied source of energy. Again, it should be noted that the above-listed enzymes are exemplary and not an exhaustive list. The enzymes can be naturally present in the eye, or can be added to the eye together with or separate from the chemical reducing agent or energetic means disclosed herein. As such, other chemically and biologically comparable enzymes that help break disulfide bonds or behave similarly should be considered as within the scope of the present invention.

In one embodiment of the invention, the reduction of disulfide groups of the lens proteins to sulfhydryl groups is accomplished by delivering to the lens a compound such as glutathione, thiols, dithiothreitol (DTT), thioredoxin, or others in sufficient quantities to reduce the disulfide bonds and other molecular and cellular adhesions. Other enzymes or chemicals that affect a methylation on the free sulfur atom include for example, methyl-methane thiosulfonate, methyl glutathione, S-methyl glutathione, S-transferase and other biologically compatible methylating agent. Use of emulsions such as nanocapsules, albumin microspheres, carrier molecules such as inositol, taurine, or other biologically suitable means such as virus phages for delivering the reducing agent or enzymes to the lens can also be used as part of this invention. The chemical reducing agent will typically be delivered in the form of a solution or suspension in an ophthalmically acceptable carrier. In some cases, the application of energy to affect or catalyze the reduction of the disulfide bonds as well as the disruption of other bonds and adhesions may be beneficial. The application of energy alone can be used to break the disulfide bonds.

Applied energy can have any form, by way of example only, any of laser, ultrasound, tuned and focused ultrasound, particle beam, plasma beam, X-ray, ultraviolet, visible light, infrared, heat, ionizing, light, magnetic, microwave, sound, electrical, femtosecond laser, tuned femtosecond laser, or other not specifically mentioned, can be used alone or in combination with the reducing agents to treat presbyopia, or a combination of any of these types of energies.

Tuning the energy source can cause disruption of the offending bonds and adhesions without the destruction of adjacent tissues and living lens fibers. This energy can be delivered by means of an apparatus external to the eye, or by way of a probe or delivery system attached to the apparatus whereby the probe is placed inside the eye through a small incision through either the cornea or the sclera. The energy can be delivered in a manner that the sum of the energy in an unit of the applied radiation is necessary to break the offending biochemical bonds. As an example only, the energy necessary to break the disulfide bond is about 12 kiloelectron volts (keV). This would be in the ultraviolet range of the light spectrum. Ultraviolet light may not pass through the cornea, so light in the 6 keV range, which is visible light, could be used to pass through the cornea and lens capsule and then through an additive effect, cause the breaking of the disulfide bonds. To fully employ this two photon hit energy transfer, the photons must be delivered in a great enough density and in a volume of space that is close enough to add their individual energies. Again, this is meant as an example only, and the system may require more than a two photon additive effect to deliver the energy necessary to break the offending bonds.

In a similar manner, agents can be delivered to the lens capsule that bind or interact with the capsule to promote greater elasticity or distendsibility. Such agents either cause the capsule to shrink in surface area or increase the tension of the lens capsule on the peripheral anterior or posterior of the lens. Applied energy can have any form, by way of example only, any of laser, ultrasound, heat, particle beam, plasma beam, X-ray, ultraviolet, visible light, infrared, ionizing, light, magnetic, microwave, sound, electrical, tuned femtosecond laser, or other not specifically mentioned can be used alone or in combination with the reducing agents to affect the treatment of presbyopia or a combination of any of these types of applied energy.

In another embodiment of the invention, applied energy can be used as a catalyst to induce or increase the rate of the reduction reaction. Thus, by applying energy, the peripheral portion of the capsule is preferentially affected, leaving the central 4 mm zone of accommodation unaffected. Or, by applying energy, the anterior portion of the lens is preferentially affected, altering the central 4 mm zone especially. This allows the lens to assume a more accommodative state. The applied energy can also be applied alone to promote the reduction reaction and the cellular changes that ultimately affect the lens' cortex. As examples, lasers useful in the present invention include: excimer, argon ion, krypton ion, carbon dioxide, helium-neon, helium-cadmium, xenon, nitrous oxide, iodine, holmium, yttrium lithium, dye, chemical, neodymium, erbium, ruby, titanium-sapphire, diode, femtosecond or attosecond laser, any harmonically oscillating laser, or any other electromagnetic radiation. Exemplary forms of heating radiation include: infrared, heating, infrared laser, radiotherapy, or any other methods of heating the lens. Finally, exemplary forms of sound energy that can be used in an embodiment of the invention include: ultrasound, any audible and non-audible sound treatment, focused ultrasound, and any other biologically compatible sound energy.

In still another embodiment of the present invention, radiation, such as ultraviolet light, visible light, infrared, microwave, or other electromagnetic energy, may be placed or directed into the eye to help break the disulfide bonds. This would then make it possible for the reduction of the disulfide or other causative bonds to occur. This reduction may occur through the use of various applied reducing agents, preferably in the form of an eye drop, but may also simply use the reducing agents already within the lens, thereby affecting the reduction reaction with applied energy alone.

The applied energy used with various embodiments and methods of the present invention could be applied through either contact with the sclera or cornea, non-contact techniques, or through intraocular methods of delivery using a probe or other such delivery device. More than one treatment may be needed to effect a suitable increase in the accommodative amplitude. When more than one modality of treatment is desirable, the chemical treatment can be administered prior to, after, or simultaneously with the application of energy, or without the application of energy depending upon the chemical reducing agent used.

In an exemplary embodiment, a treatment can comprise administering a composition of one or more active agents suspended in biocompatible carrier. In another exemplary embodiment, the active agents can be administered in a solution or suspension containing ophthalmically acceptable sterile viral phage. The phage can be introduced to the lens by, for example, topical eye drop or administered systematically as a pill or as an injection into either the blood stream or the lens itself. The carrier can include, for example, balanced salt solution or saline. The active agents can include thiol transferase in an amount of 0 to 20% by volume, preferably 2 to 10% by volume; glutathione in an amount of 0 to 20% by volume, with a preferred range of 2 to 10% by volume; and nicotinamide adenine dinucleotide phosphate (NADP) in an amount of 0 to 20% by volume, with a preferred range of 2 to 10% by volume. The balance can comprise a biocompatible carrier. The composition can be administered in total drop volumes of 0.1 to 2.5 ml with a preferred range of 0.25 to 1 ml.

In another embodiment, thiol transferase can be altered to become photo reactive. Upon administering the composition having thiol transferase (2-10% by vol.), glutathione (2-10% by vol.), or NADP (2-10%), a focused energy source such as laser can be applied to activate thiol transferase and to subsequently reduce the disulfide bonds.

Embodiments of the present invention further relate to a pharmaceutical or biologic agent capable of crossing an outer surface of an eye to affect an accommodative ability of the eye by decreasing aberrant lenticular bonds in the eye. More specifically, the pharmaceutical or biologic agent may be capable of penetrating the cornea and affecting the eye to increase its accommodative ability, both with and without the addition of an energy source. Still more specifically, the pharmaceutical or biologic agent may affect the anterior lens surface of the eye to increase accommodation. The pharmaceutical or biologic agent may act to decrease or eliminate the aberrant biochemical bonds responsible for the loss of elasticity in the lens. As discussed earlier, such aberrant biochemical bonds may cause adhesion between lens fibers, leading to reduced elasticity and accommodative ability of the lens. The aberrant biochemical bonds may include or be formed by, as an example only, covalent attachments of a variety of sugar resides to form glycoproteins, the addition of phosphate groups ($PO_4^{2-}$) or sulfate groups ($SO_4^{2-}$) to tyrosine (one of the amino acids that make up most proteins), or disulfide bonds between neighboring cysteine amino acids. The aberrant biochemical bonds may include any kind of oxidized bond, of which disulfide bonds are only one example.

In embodiments, the pharmaceutical or biologic agent may be a pro-drug. The meaning of "pro-drug" as used here includes having the property of being changeable from an inactive state to an active state. In its inactive state, a pro-drug may be able to cross a membrane of the body more easily than in its active state, making the inactive pro-drug more easy to deliver to a specific site. Once at the site, however, the pro-drug may be caused to assume an active state that allows the pro-drug to generate whatever therapeutic effect it is intended for. Activating the pro-drug, i.e., causing the pro-drug to assume the active state, may involve altering the chemical properties of the compound or compounds constituting or present in the pro-drug. Thus, the meaning of "pro-drug" further encompasses having the capability of being converted or transformed from a first biochemical or pharmacological substance to a second biochemical or pharmacological substance with properties different from properties of the first substance.

In the case of the eye, a reducing substance may be applied in pro-drug form to the outer eye, for example in a drop of liquid. The pro-drug may be in an inactive state when initially applied. The inactive state of the pro-drug may enable the pro-drug to more easily cross from the outer surface of the eye into the inner eye than would be the case it the pro-drug were in an active state. More specifically, the pro-drug may cross from the outside of the cornea to inside the aqueous humor of the eye. The pro-drug may further have solubility or acid/base properties, for example, that enable it to cross the corneal boundary. An example of a pro-drug agent is N-acetylcarnosine. Substances such as N-acetylcarnosine have the ability to cross the cornea and then be converted into other agents, such as carnosine, in the anterior chamber.

Once inside the eye, the pro-drug may be activated/converted. In its active state/converted form, the pro-drug may act as a reducing agent. To this end, the pro-drug in its active state may comprise reducing compounds. The transition of the pro-drug from its inactive state to its active state may be caused by one or more of a number of factors. For example, naturally occurring enzymes in the aqueous humor of the eye could cause the transition. Alternatively or additionally, energy could be applied externally as described earlier. That is, radiation, sonic or electromagnetic energy, heat, chemical, particle beam, plasma beam, enzyme, gene therapy, nutrients, other applied energy source, and/or any combination of any of the preceding could be applied. The applied energy may both cause a transition of the pro-drug from an inactive state to an active state, and break the aberrant biochemical bonds believed responsible for the inelasticity of the lens. The active pro-drug may then work to reduce the broken bonds. The active pro-drug may in particular be a substance for which the lens has an affinity, so that the lens actively takes up the pro-drug once past the cornea and inside the eye.

According to further embodiments of the present invention, an enzyme or enzymes may also be introduced into an eye in pro-drug form. For example, a large enzyme, such as thiol reductase, could by applied in an eye drop. In the eye drop, the large enzyme may be in a disassembled form, rendering it inactive. The disassembled form of the enzyme may make it easier for the enzyme to cross the corneal boundary into the inner eye and be taken up by the lens. Once in the inner eye, the enzyme could be activated. Here, activation may involve the re-assembly of the enzyme constituents. Activation may be brought about through the use of various externally applied forms of energy, as discussed above, or by way of the various intralenticular enzymes already present within the lens. Once assembled within the lens, the enzyme may act to promote a reduction reaction by breaking aberrant biochemical bonds including but not limited to disulfide bonds, and transferring a reducing molecule (proton) from a reducing compound to the broken bonds to prevent reformation of the bonds. Accordingly, a reducing agent to supply the reducing molecule may be introduced concurrently with the enzyme. Alternatively, the reducing agent may be introduced before or after the introduction of the enzyme. The reducing agent may be in pro-drug form.

According to alternative embodiments of the present invention, a pharmaceutical agent capable of affecting the eye's accommodative ability may be introduced by direct injection. The pharmaceutical or biologic agent may include an enzyme or enzymes to promote a reduction reaction and/or a reducing substance. The injection may be, for example, directly into the lens or into the anterior chamber, into the vitreous or the posterior chamber. The approach for this injection may be, for example, through the cornea or through the sclera. The injection may be followed by the external application of energy to further promote a reduction reaction.

If not injected into the lens but instead, for example, into the aqueous humor, the injected substance may be capable of crossing a lenticular capsular boundary into the lens. For example, the injected substance may be a substance for which the lens has an affinity, so that the lens actively takes up the substance once inside the eye. The injected substance may further be capable, upon entering the lens, of being converted into a second substance capable of affecting an accommodative ability of the eye, such as a reducing substance.

Since most of the naturally occurring lens shape alteration occurs in the central anterior portion of the lens when the eye refocuses from distant objects to near objects, lessening of aberrant lenticular bonds may be particularly beneficial when it occurs at the anterior central lens, and more specifically at the region of the anterior central lens that changes its topography during accommodation. The anterior central region of the lens is also the most easily reached by both drugs and by application of energy. Thus, embodiments of the present invention relate to specifically targeting the anterior central region of the lens for treatment. On the other hand, embodiments of the present invention further relate to specifically targeting regions outside of the anterior central region of the lens for treatment. Still further, embodiments of the present invention relate to specifically targeting the anterior central region of the lens as well as regions outside of the anterior central region of the lens for treatment.

Targeting applications according to embodiments of the present invention may include, for example, applying a reducing substance to an eye in a non-selective or non-targeted fashion, for example with an eye drop. The reducing substance may be capable of crossing the corneal boundary into the inner eye. Then, energy may be applied to only a selected portion of the lens, such as the anterior central region of the lens. In such targeting applications, the reducing agent could be formulated so that it was inactive to reduce aberrant lenticular bonds in the absence of the application of energy, but so that, when energy was applied, the reducing agent became activated and able to reduce broken lenticular bonds. Thus, the targeted, focused, and/or tuned application of energy can break lenticular bonds in a selected portion of the lens and/or also activate a reducing agent present in the selected portion. By applying energy in a highly directed manner, various optical and refractive aberrations of the lens may also be addressed and remedied. Such aberrations include but are not limited to regular astigmatism, irregular astigmatism, spherical aberrations, coma, trefoil, and other higher order optical distortions. In this manner, the lens and thereby the eye, could be restored to a level of accommodation and focus far beyond the pre-treatment level. A reducing agent with the latter properties could be obtained by one skilled in the art, for example, by suitably selecting the agent, by suitably formulating constituent compounds of the agent, by suitably controlling the concentration of the agent or of respective constituent compounds thereof, or by any combination of the foregoing. The reducing agent could be, for example, a pro-drug. On the other hand, the reducing agent could be in active form as applied, be capable of crossing the corneal boundary into the inner eye, and not require the application of energy to become active.

Targeted treatment as described above addresses an important consideration involved in the treatment of presbyopia by decreasing or lessening aberrant lenticular bonds, in that there are many important and necessary bonds in the lens that should not be altered. For example, the disulfide bond is one of the fundamental protein bonds responsible for much of the three-dimensionality of enzymes and proteins. If all the disulfide bonds were eliminated (e.g., by breaking and reducing the bonds), then there would be no real three-dimensional architecture to the lens. The lens might at this point be more of a capsular bag of fluid. On the other hand, the disulfide bond, as discussed earlier, is believed to be a factor in causing presbyopia. Using targeted treatment as described above, the amount of decrease or lessening of lenticular bonds may be controlled to be within specific ranges, within specific portions of the eye, thereby preserving beneficial bonds while reducing others selectively. In one range, aberrant lenticular bonds may be decreased by 10% to 70% in targeted regions. In another range, aberrant lenticular bonds may be decreased by 20% to 50% in targeted regions.

In embodiments of the present invention, targeted treatment need not include application of a reducing agent in conjunction with the application of energy. Instead, a substance could be suitably formulated (e.g., in terms of constituent compounds, concentration, etc. as described above) so that the substance could both break aberrant biochemical bonds and reduce the broken bonds, within specific portions of the eye. For example, the specific portion could be in the anterior central region of the eye. To target a specific portion of the eye, the substance could, for example, be formulated to have an affinity for the specific portion. The amount of decrease in lenticular bonds could be controlled to be within specific ranges. In one range, aberrant lenticular bonds may be decreased by 10% to 70% in targeted regions. In another range, aberrant lenticular bonds may be decreased by 20% to 50% in targeted regions.

In embodiments of the present invention, iontophoresis may be used to help transport a reducing substance into the eye and into the lens. Application of energy may or may not be used in conjunction with the latter.

In still other embodiments of the present invention, one or more enzymes to promote or facilitate a reduction reaction may be introduced into the lens using a viral phage. The viral phage may be used to transfect the lens cells with a gene to transcribe an enzyme's genetic code into the lens cells using the RNA or DNA transcriptase already present within the lens cells, as opposed to introducing the enzyme itself. Once this genetic code was in the lens cells, the natural protein manufacturing mechanisms present in the cells would create the enzyme from the genetic code. This technique would circumvent the issue of getting large enzymes into the lens through the lens capsule. The lens could then further be treated with reducing agents in any form and applications of energy including energy targeted or focused on specific portions of the lens.

Finally, it is observed that various types of human tissues are derived from the same epithelial line of embryonic cells as the lens. The skin is one example. The skin undergoes various forms of oxidation, which leads to the typical alterations brought on by aging. Methods as described above could be applied to epithelial tissues like skin to reduce the oxidized biochemical bonds therein, such as the disulfide bonds, to thereby rejuvenate the tissues. Each of the various epithelial tissues could receive a treatment specifically designed to take into account the tissue's location and accessibility. For example, the skin can be treated directly with a reducing agent and then energy could be applied to help break the oxidized bonds. Additionally or alternatively, a combination of enzymes and catalysts can be used to stimulate the reduction reaction. Specific portions of the skin or other epithelial tissue could be treated with targeted application of energy.

The reducing agents and enzymes used to treat the skin or other epithelial tissue as described above could be applied in active form, or could have any one or any combination of the properties of the reducing agents and enzymes discussed above in connection with treatment of the eye for presbyopia. That is, the reducing agents and enzymes could be in pro-drug form, or in a form requiring the application of energy to become active, or the like.

Embodiments of the present invention further relate to methods for delivering pharmaceuticals to the lens of the eye for treating or preventing presbyopia. These methods may provide delivery of effective amounts of pharmaceuticals directly into the lens capsule and/or the lens fibers to break down disulfide bonds at the lens fibers and prevent these bonds from forming, thereby treating or preventing presbyopia.

In one embodiment, iontophoresis may be used to deliver the pharmaceutical. FIG. 1 illustrates an iontophoretic device that may be used according to methods of the present invention. Iontophoretic device 100 may include a controller 110, which may include logic, a voltage source, and other electrical components to control and deliver an electric current. Electrodes 120 may be electrically attached to the container to transmit and receive the electric current. Electrodes 120 may have conductive pads 130 for contacting and/or attaching to human tissue. As further described below, the pads 130 may be directly attached to the head and/or face prior to the beginning of delivery of the pharmaceuticals.

Iontophoresis involves applying an electric current to a charged substance to facilitate the delivery of the charged substance into human tissue. Iontophoretic electrodes 120 may be spaced apart near the location for the charged substance to be delivered. Applying an electric current between the electrodes creates an electric field whereby the charged substance travels via the electric field through the tissue.

In this embodiment, any of the pharmaceuticals as described above may first be added to a solution that is placed in a charged state by any method for ionizing solutions. The charged solution may then be administered to the eye by eye drops, eye swabs, or any other such method. The electrodes may be placed at various locations on the face or head in order to establish an electric field through the lens area of the eye. The electric current may be applied by the electrodes. The charged solution may then travel in the direction of one of the electrodes. The charged solution is drawn into the eye toward the lens, across the lens membrane, through the lens, and/or into the lens fibers and/or lens capsule by the electric field. After the pharmaceutical is delivered, the electric current may be turned off.

In another embodiment, nano-medication may be used to deliver pharmaceuticals for treating or preventing presbyopia. Nano-medication involves the delivery of pharmaceuticals in small forms, on the order of nanometer size, such that the relative amount of drug to the drug's surface area is increased. The pharmaceutical nano-molecules easily diffuse through the capillaries of the eye into the lens, lens fibers, and/or lens capsule.

In this embodiment, any of the pharmaceuticals as described above may first be processed to form nanometer sized molecules. These molecules may be formed into nano-micelles, which may be a nanometer-sized aggregation of the molecules, and encapsulated to prevent interaction prior to arrival at the desired location in the body. The nano-micelles may be administered to the eye as eye drops, eye swabs, or any other such method. Upon contact with the eye, the capillaries of the eye may readily absorb the nano-micelles containing the pharmaceutical and distribute the pharmaceutical across the lens membrane, through the lens, and/or into the lens fibers and/or lens capsule.

Upon arrival at the lens fibers and/or lens capsule, the nano-micelle capsule may dissolve, and the released pharmaceutical may have a therapeutic effect on the lens fibers and/or lens capsule.

In another embodiment, photonic activation may be used to deliver pharmaceuticals for treating or preventing presbyopia. In this mechanism, photons may be directed to an inert substance, thereby activating the substance. Photons may be applied by a laser, an LED, or any other incoherent light source.

Figure 2:
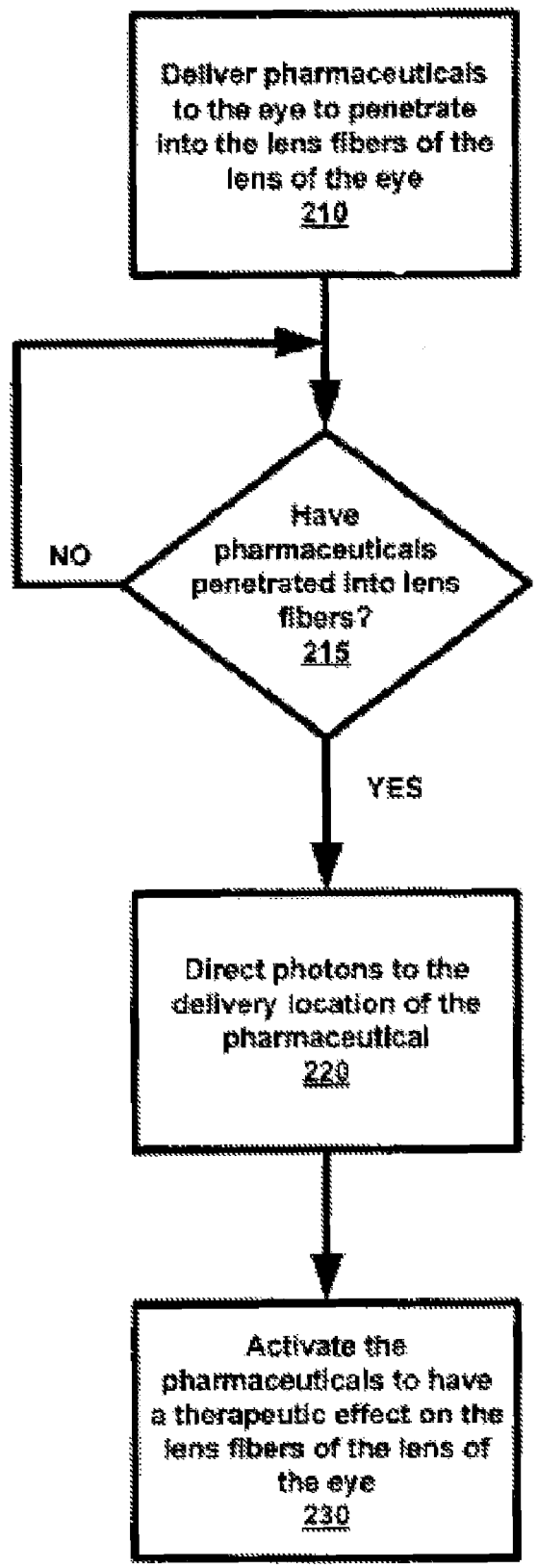
FIG. 2 is a flowchart of a method for delivering pharmaceuticals by photonic activation.
Figure 3:
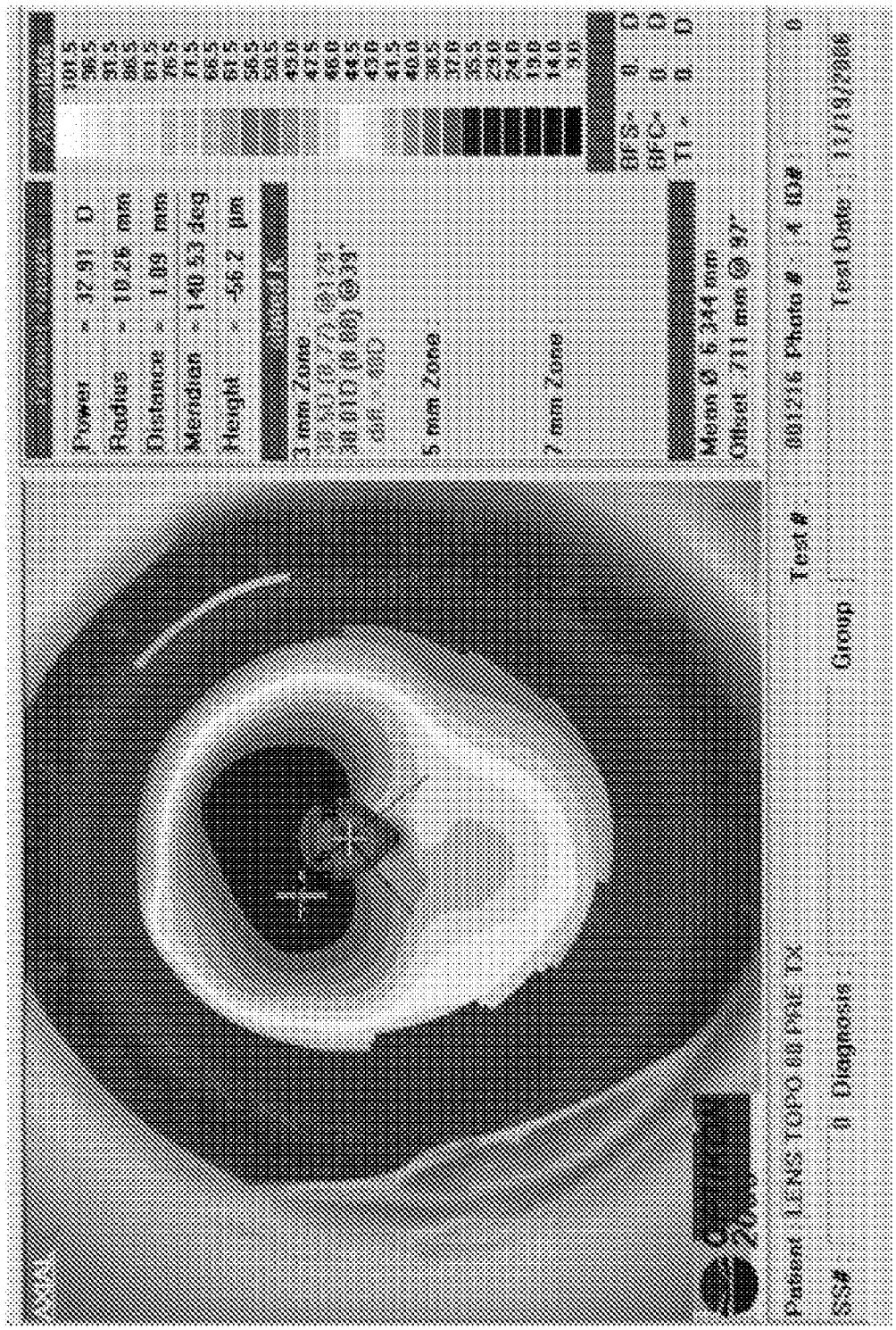
FIG. 3 shows pre-treatment lens topography.
Figure 4:
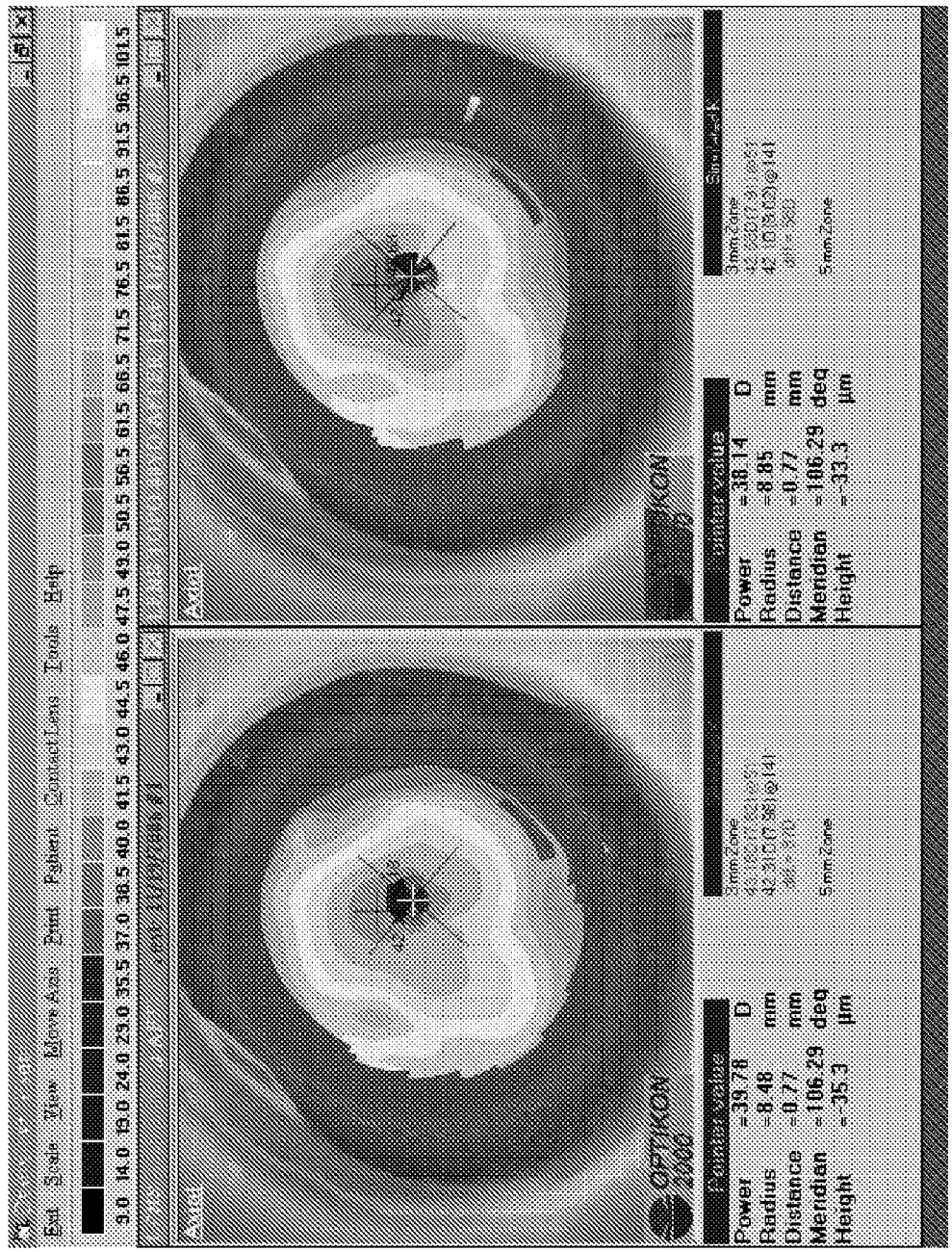
FIG. 4 shows the lens topography 5 minutes after treatment with DTT.
Figure 5:
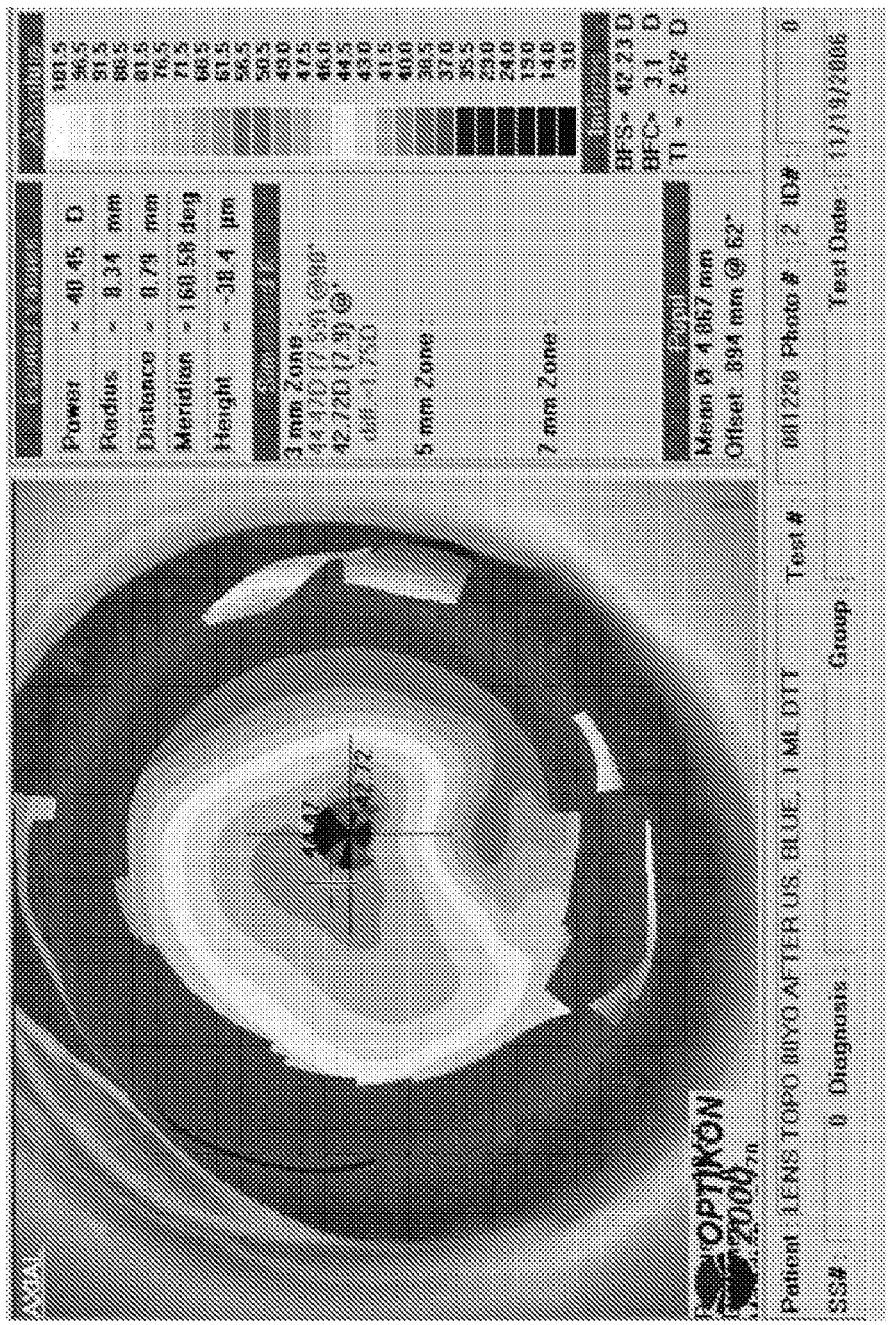
FIG. 5 shows the lens topography 15 minutes after treatment with DTT.
Figure 6:
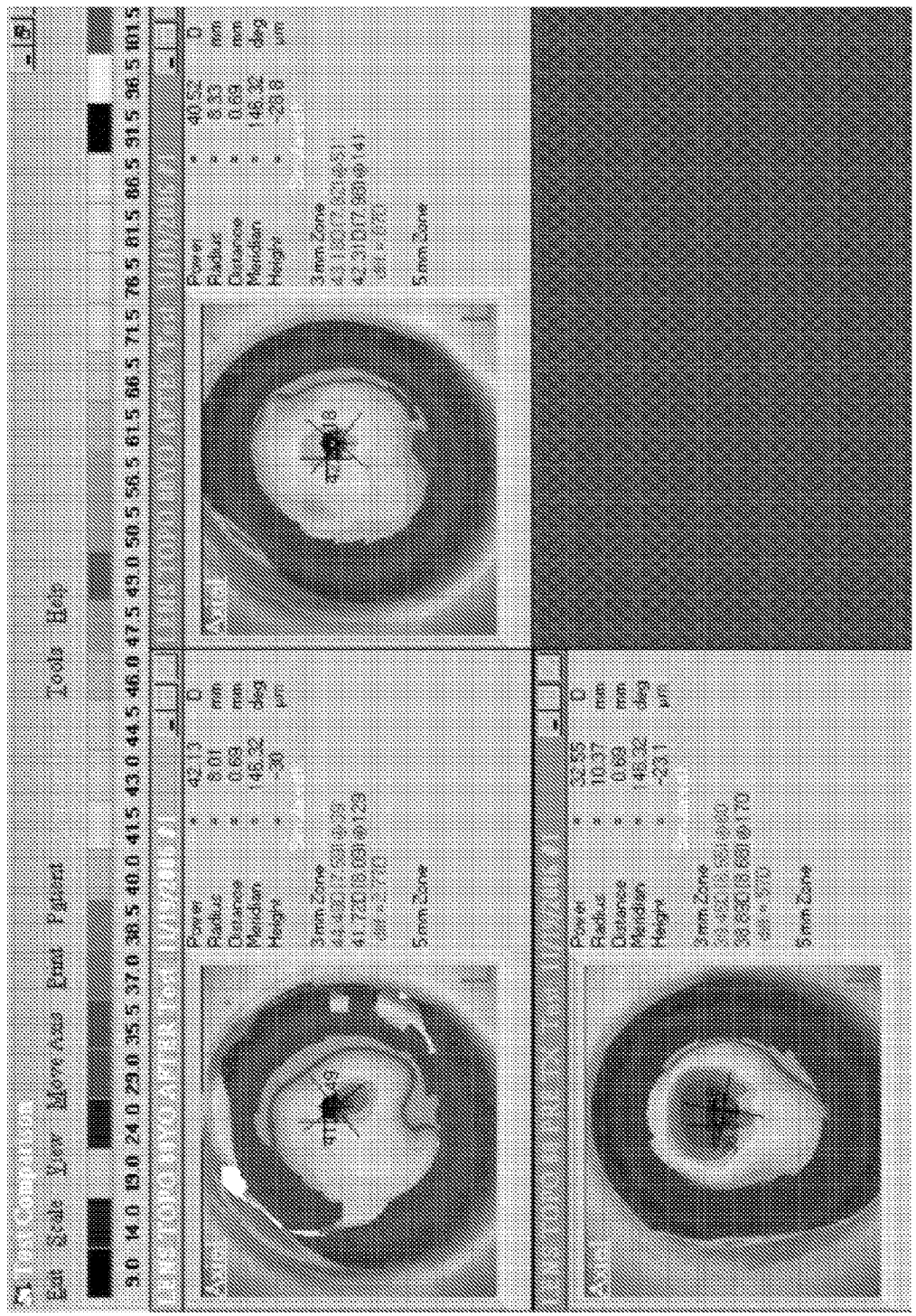
FIG. 6 shows comparative lens topography.

FIG. 2 is a flowchart of a photo activation method for delivering pharmaceuticals for treating or preventing presbyopia. The inert substance may be administered to and dispersed (210) into human tissue. After the substance arrives (215) at the desired location in the body, photons may then be directed (220) to the inert substance. Upon contact with the photons, the inert substance may activate (230) so as to affect the human tissue into which the substance dispersed. The inert substance may include compounds that may be activated by selective wavelengths of light, selective absorption of light, e.g., exogenous chromophores, and other such techniques.

In this embodiment, a pro-drug of any of the pharmaceuticals as described above may be used. As described above, a pro-drug is a pharmaceutical that may be formulated in an inert state, i.e., being chemically structured so as not to have a therapeutic effect, and then changeable from the inert state to an active state to exert its effects. In its inert state, a pro-drug may be able to penetrate human tissue more easily than it its active state because the drug may not interact with the penetrated tissue as the drugs contacts it. Hence, the inert pro-drug may be easier to deliver in effective amounts to a specific site in the tissue. Once at the site, the pro-drug may be activated to generate its therapeutic effect. In this embodiment, the pro-drug may be activated by photons. Activating the pro-drug may involve altering the chemical properties of the components of the pro-drug, e.g., breaking the chemical bonds of the pro-drug to form a different pharmaceutical substance with different properties.

The pro-drug may be administered to the eye as eye drops, eye swabs, or any other such method. The pro-drug may then be absorbed into the eye toward the lens, across the lens membrane, through the lens, and/or into the lens fibers and/or lens capsule. Photons may be then be directed to the pro-drug, activating the pro-drug. The active pro-drug may then perform its therapeutic function on the lens fibers and/or lens capsule.

Photons may be directed so as to provide a differential gradient of activation. That is, the pro-drug in one location of the eye may be more active than the pro-drug in another location of the eye by providing different levels of photonic energy to those locations.

One of the unique aspects of this invention is the safety of the treatment in that the living tissues are not vaporized or destroyed in the process of the reduction of the offending bonds. The treatment is repeatable throughout a patient's life as necessary in a manner that can continue to deliver the needed augmentation of a patient's accommodation without harming the lens or other eye tissues. This invention treats the actual cause of the loss of accommodation and not altering other structures or tissues in the lens. Thus, in one embodiment, the method increases accommodative amplitude without causing substantial damage to the living lens fibers and tissues. While the breaking of bonds may have some affect on healthy tissue, the methods described herein can treat presbyopis without causing substantial damage to healthy tissue. In other words, the methods can maintain one or more optical properties of the lens, e.g., lens transparency and optical power.

Several embodiments of the present invention are specifically illustrated and described herein. However, it will be appreciated that modifications and variations of the present invention are covered by the above teachings and within the purview of the appended claims without departing from the spirit and intended scope of the invention.

Example 1

Breaking Aberrant Disulfide Bonds with DTT

An 80 year-old preserved cadaver eye was sectioned such that the anterior segment consisting of the cornea, aqueous, and iris was removed, and 0.1 cc of a 1.0 molar concentration of DTT was used to treat the human lens. The DTT was allowed to react with the lens through the intact capsule for five and fifteen minutes. During this time span, the lens was periodically rewetted with balanced salt solution to prevent any drying out of the lens.

The anterior lens curvature lens was measured using an inventive modified topography device (Keratron) used originally in the horizontal position for measuring corneal curvature. The inventive topography device was positioned in the vertical position such that the crystalline lens being measured could be positioned also in the vertical facing up with its anterior capsule facing the inventive topography device. This allowed for the eye's lens to remain for the most part within the eye undisturbed while the DTT was added and the topographical measurements were made. And further it should be noted that the ciliary body, ciliary muscle, lenticular zonules, lenticular capsule, vitreous were all still connected.

The inventive lens topography device was positioned such that it would focus lighted mires on the anterior surface of the lens. Lenticular topography measurements were performed prior to treatment with DTT and at the five- and fifteen-minute marks. Substantial increases in the curvature of the lens were noted at the five-minute period as well as additional steepening at the fifteen-minute mark. In addition, the mires could be seen to become more visible, better defined, with increased contrast and more spherical during the period beginning with the instillation of the DTT and the conclusion of the experiment. Calculations of the measurements made showed the increase in accommodative power of the lens to be from 0 diopters up to about 1.8 diopters in situ as opposed to 8 to 10 diopters in air. Looking at representative lenticular topography readings in the identical location in the pre-treatment, after 5 minute, and after 15 minutes, the change as shown in the comparison topography is from 32.55 D to 42.13 D or 9.58 D in air.

Thus in the experiment from the time of the first addition of DTT onto the anterior surface of the lens capsule, there was an increase in accommodation starting from no change prior to the addition of DTT, and then following the instillation of DTT there was a change of curvature which would translate with time into an increase of accommodation of +0.25 D, then +0.50 D, then +0.75 D, then +1.00 D, then +1.25 D, then +1.50 D and ending with +1.80 D. While the preceding is expressed in mostly +0.25 D increments of increase, in actuality the increments occurred in a progression of fractions of a diopter increments, by way of example only 0.12 D or less, until it reached 1.80 D of increase.

DTT softened the lens. The softening could be felt by direct palpitation of the treated lens following the conclusion of the experiment.

This experiment confirms the inventor's theory as to the cause of presbyopia and proves that with the inventive treatment, it is possible to soften the lens, increase accommodation, and thus reverse and/or prevent presbyopia by way of breaking and reducing the unwanted disulfide bonds.

What is claimed is:

1. A method for increasing the accommodative amplitude of a lens comprising:

administering a pharmaceutically sufficient quantity of a biologically acceptable chemical substance to break chemical bonds, wherein the biologically acceptable chemical substance is at least one of dithiothreitol, a trialkylphosphine compound, and tris[2-carboxyethyl] phosphine hydrochloride.

2. The method of claim 1, wherein the biologically acceptable chemical substance is dithiothreitol.

3. The method of claim 1, wherein the amplitude of accommodation is increased by at least one diopter.

4. The method of claim 1, wherein administering the biologically acceptable chemical agent is performed in the absence of externally applied energy.

5. The method of claim 1, further comprising applying localized energy to an area to be treated, wherein lens transparency and/or the lens optical power is maintained.

* * * * *